US008468885B2

(12) United States Patent
Berndt et al.

(10) Patent No.: US 8,468,885 B2
(45) Date of Patent: Jun. 25, 2013

(54) DISPENSE VOLUME MONITOR FOR ARRAYS

(75) Inventors: Klaus W. Berndt, Cockeysville, MD (US); Andris J. Jaunzemis, Parkton, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 346 days.

(21) Appl. No.: 12/664,690

(22) PCT Filed: Jun. 20, 2008

(86) PCT No.: PCT/US2008/067738

§ 371 (c)(1), (2), (4) Date: Jun. 1, 2010

(87) PCT Pub. No.: WO2009/002868

PCT Pub. Date: Dec. 31, 2008

(65) Prior Publication Data

US 2010/0229642 A1 Sep. 16, 2010

(51) Int. Cl.
*G01F 23/26* (2006.01)
*G01F 17/00* (2006.01)

(52) U.S. Cl.
USPC ........................................ 73/304 C; 73/149

(58) Field of Classification Search
USPC .................... 73/149, 304 C; 346/20; 340/620
See application file for complete search history.

(56) References Cited

U.S. PATENT DOCUMENTS 5,254,311 A * 10/1993 Ushikubo ...................... 422/81
5,314,825 A * 5/1994 Weyrauch et al. .............. 436/43
6,568,264 B2 * 5/2003 Heger ........................ 73/304 C
2004/0149032 A1 * 8/2004 Sell ............................ 73/304 C
2004/0199131 A1 * 10/2004 Kitamura ...................... 604/318
2005/0019900 A1 * 1/2005 Broyer et al. .............. 435/287.1
2005/0247125 A1 * 11/2005 Williams et al. ............ 73/304 C
2006/0262101 A1 * 11/2006 Layton et al. ................. 345/173
2007/0096164 A1 * 5/2007 Peters et al. .................. 257/253

FOREIGN PATENT DOCUMENTS

JP 04158224 A 6/1992
JP 05010958 A 1/1993
JP 08146011 A 6/1996
JP 11014430 A 1/1999
JP 2003090754 A 3/2003
JP 2005513432 A 5/2005

OTHER PUBLICATIONS

Japanese Office Action for Application No. 2010-513459 dated Jul. 6, 2012.
Internatiomal Search Report for Application No. PCT/US2008/067738 dated Oct. 17, 2008.
Chinese Office Action for Application No. 200880101375 dated Apr. 29, 2011.
Chinese Office Action for Application No. 200880101375 dated Apr. 18, 2012.

* cited by examiner

*Primary Examiner* — Hezron E Williams
*Assistant Examiner* — David Z Huang
(74) *Attorney, Agent, or Firm* — Lerner, David, Littenberg, Krumholz & Mentlik, LLP

(57) ABSTRACT

The reagent volume dispensed into wells (3) of a test plate (2) is determined by moving an upper electrode (5) of specific profile into each well to an optimum position above the well bottom, by determining the capacitance value of the capacitor formed by the upper electrode in each well and a lower electrode (6) arranged adjacent to the lower outside surface (11) of the test plate below each well, and by comparing the measured capacitance value with reference calibration values.

35 Claims, 18 Drawing Sheets

1 5 3 4 2 6 11

DISPENSE VOLUME MONITOR FOR ARRAYS

FIELD OF THE INVENTION

The present invention relates to methods and apparatus for accurately dispensing a predetermined small volume of liquid reagents into open containers. In one embodiment, the present invention relates to methods and apparatus for determining the volume of liquid reagents that are dispensed into two-dimensional arrays of open wells.

BACKGROUND OF THE INVENTION

The dispensing of small volume reagent droplets with high accuracy represents an important process step in the production of medical diagnostic assays which are frequently based on using two-dimensional arrays of open wells, such as microtiter plates. Some examples of such dispense systems in use are described in the following references: U.S. Pat. No. 4,107,658, U.S. Pat. No. 4,196,615, U.S. Pat. No. 4,417,473, U.S. Pat. No. 4,818,492, U.S. Pat. No. 5,304,347, U.S. Pat. No. 5,601,980, U.S. Pat. No. 6,029,896, U.S. Pat. No. 6,148,666, U.S. Pat. No. 6,213,354, U.S. Pat. No. 6,551,558, U.S. Pat. No. 6,823,730, U.S. Pat. No. 6,851,778, U.S. Pat. No. 6,875,404, US 2001/0016177 A1, WO 98/09151, WO 00/51736, WO 01/89694 A1, WO 02/26499 A1, WO 03/106936, EP 0,164,679, EP 0,355,791, EP 0,505,004, EP 0,725,267, JP 2004251818 A, JP 2006058188 A.

However, the accurate determination of volume actually dispensed into each of the individual wells in an array still remains a problem.

In needle-based dispensing systems, the targeted amount of liquid leaving the inner needle space is, in many cases, very well controlled, e.g. by the specific motion of a dispensing piston, by utilizing specialized pumps with accurate dosing capability, or by application of piezo-electric devices producing a defined volume displacement. However, the amount of liquid actually reaching the receiving well may vary, because part of the liquid leaving the inner needle space is creeping along the outer diameter of the dispensed needle, therefore forming a small amount of liquid that is lost from the particular dispense act. This mechanism may repeat itself in one or more successive dispense acts and a substantial amount of liquid may, consequently, accumulate on the outer needle diameter. Once a critical amount of liquid accumulates, this liquid will join a dispensed droplet, generating an actual dispensed volume that significantly exceeds the targeted dispensed volume.

In certain dispensing arrangements, where the dispense mechanism cannot generate adequate shear force to cleave a droplet, the dispensed droplet is not ejected freely into the air space, but is brought into contact with the bottom of the receiving well, while still in contact with the dispensed needle. This mode of dispensing, which is called touch-off mode, offers a chance for obtaining a very even distribution of dispensed liquid on the well bottom, in particular for droplet volumes below 10 μL. The touch-off dispensing mode may also promote a certain amount of liquid collecting and creeping upwards on the outer diameter of the dispensed needle if optimum touch off conditions are not maintained.

When sample liquid is aspirated into a dispense needle, the needle has to contact the liquid in the supply reservoir. When needle is withdrawn from the reservoir after the aspiration step, residual liquid from the supply reservoir may remain on the outside of the dispense needle. It is also likely that such liquid may join the dispensed liquid in a dispensing step that follows the aspiration step, creating a droplet of incorrect volume.

Therefore an apparatus and method is required for an accurate determination of the liquid reagent volume actually dispensed into each individual well in a two-dimensional open well array.

SUMMARY OF THE INVENTION

The various embodiments of the present invention overcome the above stated problems by providing a method and dispense volume monitor apparatus for accurately determining the liquid reagent volume dispensed into, for example, each individual well of a test plate. As used herein, the term test plate means a two-dimensional array of open wells within an electrically non-conductive tray, for example, a microtiter plate, a tissue culture plate, a disposable or the like, although other configurations may be available.

According to one embodiment of the present invention, a dispense volume monitor comprises electrode configuration including an first electrode connected to a signal source, positioned adjacent or in a well of a test plate and a second electrode arranged adjacent to the bottom exterior surface of the test plate, below the well, connected to the input of an RF voltmeter, thus forming at least one capacitor.

In another further embodiment, the present invention provides a dispense volume monitor, a capacitance value of which is primarily derived from the volume of dispensed liquid reagent within a well, and which accounts for the effect of meniscus shape on said capacitance value. This may be achieved by selecting an optimized lower profile section for the upper electrode resembling the shape of an average meniscus for the liquids dispensed.

In an additional embodiment, the present invention provides a dispense volume monitor, a capacitance value of which depends only to a lesser degree on the dielectric constant of the dispensed reagent sample in a well. This may be achieved by inserting the aforementioned cylindrical upper electrode of a specific profile coaxially into each well to a defined position above the well bottom such that the overall capacitance is predominantly determined by the air space between the upper electrode and the surface of the dispensed liquid in a well, and only to a much lesser degree by the capacitance of the liquid component.

In another embodiment, a dispense volume monitor is provided having a plurality of upper electrodes arranged in an array of at least one row and at least one column held in place by a first electrical insulating member, a plurality of lower electrodes arranged in a matching array of at least one row and at least one column, and a test plate comprising a plurality of wells arranged in a matching array of at least one row and at least one column, such that on insertion of the plurality of upper electrodes into the plurality of wells a plurality of capacitors are formed.

In addition, this embodiment may further include a multiplexer and/or a demultiplexer. The multiplexer having a plurality of input channels and one output channel, wherein the plurality of lower electrodes are connected to the plurality of input channels of the multiplexer, and the output channel is connected to an input of a voltmeter. The demultiplexer having one input provides channel and a plurality of output channels, wherein the input channel is connected to an output of a signal source and a plurality of upper electrodes are connected to the output channels of the demultiplexer.

Another embodiment of the present invention provides electrical circuitry for a two-dimensional array of dispense volume monitors allowing interrogation of all wells in a two-dimensional array within a short period of time. This may be achieved either by applying an RF drive signal simultaneously to all upper electrodes in the array, and interrogating the lower electrodes via a low input impedance multiplexer, or by applying an RF drive signal in a serial mode of operation to all upper electrodes in the array via a low output impedance demultiplexer, and connecting all lower electrodes in parallel with an RF detector.

A further embodiment of the present invention provides electrical circuitry for a two-dimensional array of dispense volume monitors allowing interrogation of all wells in a two-dimensional array with a demultiplexer and multiplexer of relatively low channel numbers. This may be achieved by applying an RF drive signal in a mixed mode of operation to all upper electrodes in the array via a demultiplexer with relatively low output impedance values and having a low number of channels addressing one row at a time, whereby all electrodes in a row are connected with each other, and interrogating the lower electrodes via a multiplexer with relatively low input impedance values and having a low number of channels addressing one column at a time, whereby all electrodes in a column are connected with each other.

A further embodiment provides a method for accurately determining the volume of liquid reagents actually dispensed into each well in a test plate, including the steps of inserting a first electrode into a container, wherein the container comprises a dispensed liquid sample volume, and a second electrode is arranged adjacent to the lower outside of the container, thereby forming a capacitor, and measuring the capacitance of the capacitor. The capacitance value of the dispensed liquid sample volume and the volume of the dispensed liquid sample are determined by comparing the capacitance value of the dispensed liquid sample volume with a calibration capacitance value. The calibration capacitance value is a capacitance value for a known dispensed liquid sample volume. The capacitance value of the dispensed liquid sample volume is calculated by subtracting a reference capacitance value from the measured capacitance value, wherein the reference capacitance value is the capacitance value of the capacitor with no liquid sample present in the container. A processor can be used to compare the capacitance value of the dispensed liquid sample volume with the calibration capacitance value, calculate the capacitance value of the dispensed liquid sample volume and calculate the volume of the dispensed liquid.

DETAILED DESCRIPTION OF THE INVENTION

In needle-based dispensing systems, the targeted amount of liquid leaving the inner needle space is, in many cases, very well controlled, e.g. by the specific motion of a dispensing piston, by utilizing specialized pumps with accurate dosing capability, or by application of piezo-electric devices producing a defined volume displacement. However, the amount of liquid actually reaching the receiving well may vary, because part of the liquid leaving the inner needle space is creeping along the outer diameter of the dispensed needle, therefore forming a small amount of liquid that is lost from the particular dispense act. This occurrence may repeat itself in one or more successive dispense acts and a substantial amount of liquid may, consequently, accumulate on the outer needle diameter. Once a critical amount of liquid accumulates, this liquid will join a dispensed droplet, generating an actual dispensed volume that significantly exceeds the targeted dispensed volume.

In certain dispensing arrangements, where the dispense mechanism cannot generate adequate shear force to cleave a droplet, the dispensed droplet is not ejected into the air space, but is brought into contact with the bottom of the receiving well, while still in contact with the dispense needle. This mode of dispensing, which is called touch-off mode, offers a chance for obtaining a very even distribution of dispensed liquid on the well bottom, in particular for droplet volumes below 10 μL. The touch-off dispensing mode may also promote a certain amount of liquid collecting and creeping upwards on the outer diameter of the dispense needle if optimum touch off conditions are not maintained.

When sample liquid is aspirated into a dispense needle, the needle has to contact the liquid in the supply reservoir. When needle is withdrawn from the reservoir after the aspiration step, residual liquid from the supply reservoir may remain on the outside of the dispense needle. It is also likely that such liquid may join the dispensed liquid in a dispensing step that follows the aspiration step, creating a droplet of incorrect volume.

This behavior is applicable to most types of liquids, including the types of liquids and reagents utilized in the production of medical diagnostic assays such as microorganism identification (ID) and antimicrobial susceptibility determinations (AST), which may be a water based solution/suspension or a hydrocarbon based (e.g. ethanol) solution/suspension. A typical range of the target dispense volume is 0.5 μm to 100 μm. The type of container in which the liquid is dispensed into is typically a two-dimensional array of open wells, such as microtiter plates or test plates, however any small volume container is applicable.

Apparatus and methods for an accurate quantification of the liquid reagent volume actually dispensed into each individual well in a two-dimensional open well array are described below in accordance with certain embodiments of the invention.

Figure 1:
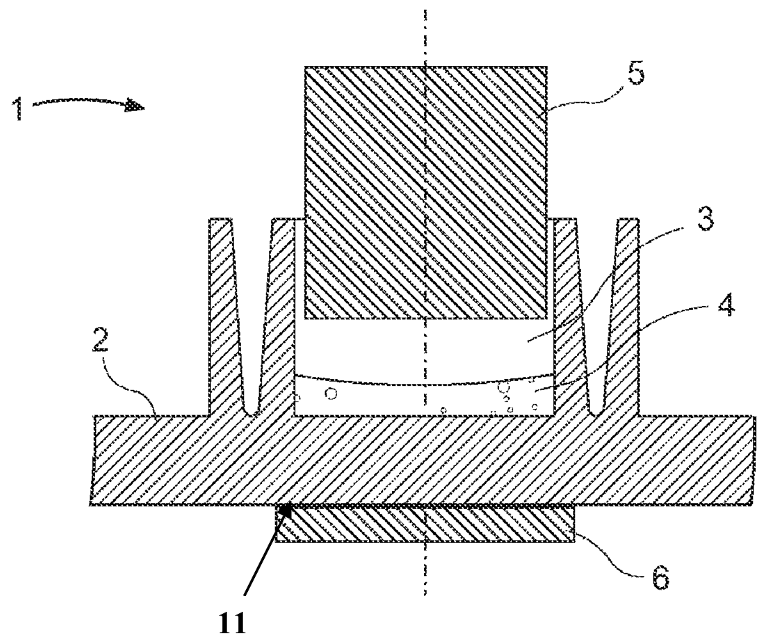
FIG. 1 is a cross sectional view of a cylindrical electrode configuration in accordance with an embodiment of the invention.

A portion of a dispense volume monitor in accordance with an embodiment of the invention is illustrated in FIG. 1. The sensor, in this case, is a cylindrical electrode configuration. Cylindrical electrode configuration 1 contains a first upper electrode 5 positioned into well 3 of the two-dimensional array of open wells within an electrically non-conductive tray i.e. a test plate 2. Well 3 contains a dispensed liquid volume 4, which in the context of the present invention may occupy only a relatively small percentage of the overall volume of well 3. The cylindrical electrode configuration 1 is comprised of a second lower flat electrode 6 arranged adjacent to the exterior bottom surface 11 of test plate 2, below the well 3. It should be noted that second electrode 6 does not have to be permanently connected with test plate 2, e.g. by using an adhesive, but must be positioned in proximity to the exterior bottom surface 11 of test plate 2 below the well 3. In other words, this means that a dispense volume monitor, according to an embodiment of the present invention, is able to tolerate small and unpredictable air gaps in the tens-of-μm-range between the exterior bottom surface 11 of test plate 2 and second lower electrode 6. This tolerance aspect allows a large number of test plates to be placed serially into a sensing station comprising of an array of lower electrodes 6, and inserting an array of upper electrodes 5 into the matrix of open wells 3 to perform dispense volume measurements in all wells 3 of the test plate 2.

Figure 29:
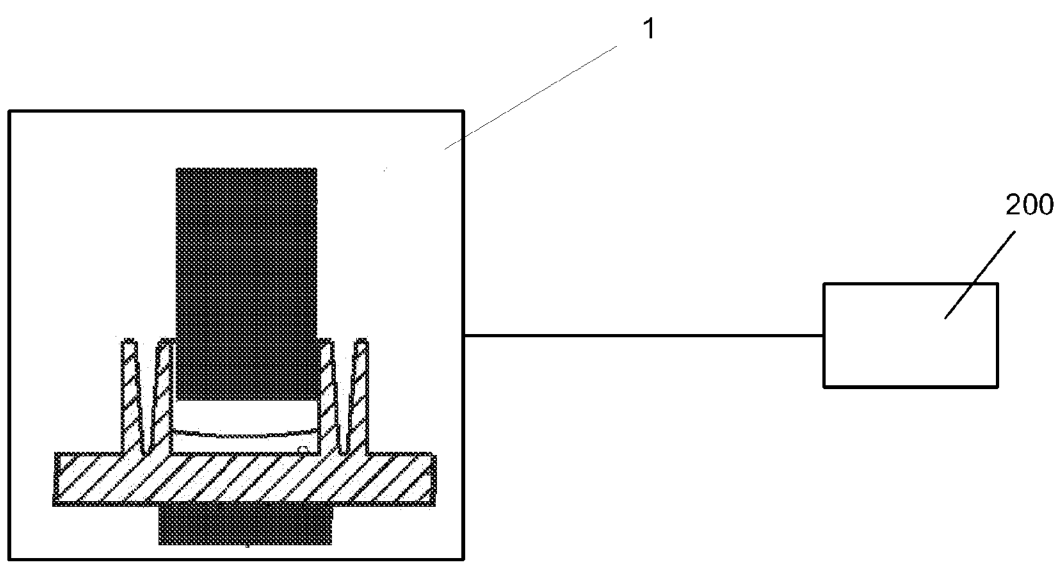
FIG. 29 illustrates a functional schematic depicting the cylinder capacitor arrangement of FIG. 1 in communication with a processor, in accordance with an embodiment of the invention.

According to an embodiment of the present invention, the volume of dispensed liquid 4 in FIG. 1 is measured by determining the capacitance value of cylindrical electrode configuration 1, and by comparing the measured capacitance value with reference capacitance values determined earlier for known dispensed liquid reagent volumes. The comparison of the capacitance values may be accomplished by, for example, a processor or comparator 200. FIG. 29 illustrates a functional schematic depicting the cylinder capacitor arrangement of FIG. 1 in communication with a processor 200, in accordance with an embodiment of the invention.

Pursuant to embodiments of the present invention, an electrode configuration 1 is provided that yields a capacitance value primarily derived from the magnitude of the dispensed liquid volume 4 within a well, and which reduces the effect of the dielectric constant of the dispensed liquid and the upper surface shape of the dispensed liquid volume on the capacitance value of electrode configuration 1.

Liquid reagent solutions are frequently based on solvents such as water or ethanol (ETOH). These solvents may have very different dielectric constants. Nevertheless, embodiments of the present invention provide an electrode configuration 1 the capacitance value of which depends only to a lesser degree on the dielectric constant of the dispensed liquid volume 4 in a well. This may be achieved by inserting said cylindrical upper electrode 5 of specific profile coaxially into each well to a defined position above the well bottom such that the overall capacitance value is predominantly determined by the air space between upper electrode 5 and the surface of the dispensed liquid 4 in a well, and only to a much lesser degree by the dielectric constant of the liquid component 4.

Dispensed liquid volume 4 in FIG. 1 is expected to develop a curved upper surface area, which is called a meniscus. The exact shape of the meniscus will depend on characteristic material parameters of both the dispensed liquid volume 4, (e.g. viscosity), and the test plate 2, (e.g. surface energy). It is known within the art to expose the inner wall and the bottom of well 3 to a corona treatment, which promotes adhesion of the liquid 4 to the walls and bottom of the well, and to achieve a symmetrical distribution of liquid sample 4 within well 3.

The effect of the meniscus shape of the dispensed liquid volume 4 within a well on the capacitance value, may be mitigated by selecting an upper electrode 5 having a diameter that is smaller than the diameter of well 3, and by selecting an optimized lower profile section for upper electrode 5 that resembles the shape of an average meniscus for the liquids to be dispensed. A diameter for upper electrode 5 corresponding to 80% or less of the well diameter is advantageous. Electrodes with a diameter of 60% or even less are typically suitable, and provide capacitance values determined with the appropriate precision within a short period of time.

A well as shown in FIG. 1 may for example have a diameter of 3.66 mm and a height of 2.8 mm so that the overall volume of the well is 29.4 μL. The target volume to be dispensed may be 5 μL, which corresponds to only 17% of the overall well volume. A dispensed liquid sample having a totally flat meniscus shape would, in this case, fill the well up to a height of 0.476 mm. According to an embodiment of the present invention, the lower end 30 of upper electrode 5 could be positioned at a height above the well bottom between 50% and 30% of the well height, i.e. at 1.4 mm or 0.84 mm, respectively. At a height of 50%, the air gap is conveniently large to avoid any danger for the liquid sample 4 coming into contact with upper electrode 5. At a height of 30%, this risk may be slightly higher, but the sensitivity of the dispense volume monitor will be higher. Shaping the lower profile section of upper electrode 5 in a way similar to an average meniscus shape makes not only the capacitance value less dependent on the particular shape of the meniscus, but is also advantageous for avoiding contact between upper electrode 5 and liquid 4. These aspects of the various embodiments of the present invention are discussed in more detail below.

Figure 2:
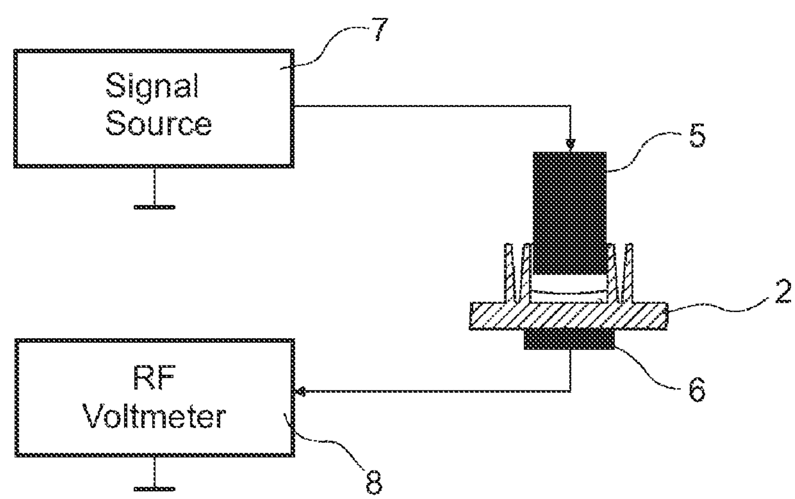
FIG. 2 shows a basic electrical configuration for determining dispense volume, according to an embodiment of the present invention.

FIG. 2 shows an electrical configuration for a dispense volume monitor, according to an embodiment of the present invention. A signal source 7 such as a sine-wave generator is connected to upper electrode 5 as introduced in FIG. 1, which is positioned into a well 3 of test plate 2. The lower flat electrode 6, which forms the second electrode of cylindrical capacitor configuration 1, is connected to the input of an RF voltmeter 8. It should be noted that a sensor according to an embodiment of the present invention is not restricted to the use of sinusoidal excitation. However, while other time-dependent periodic signals could also be used, the following detailed description of the invention assumes the use of sinusoidal signals.

Figure 3:
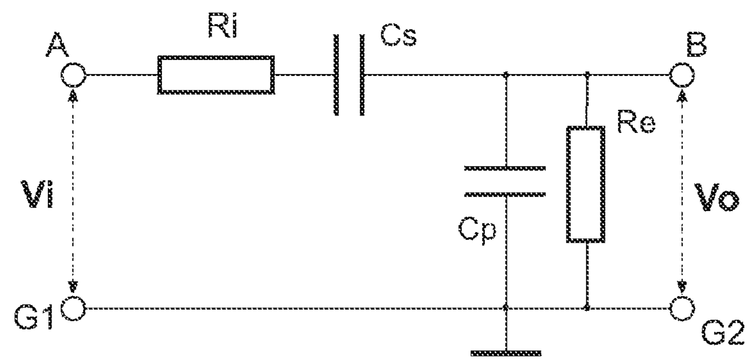
FIG. 3 depicts an electrical circuit diagram for determining the dispense volume, according to an embodiment of the present invention.

FIG. 3 shows the circuit diagram for a dispense volume monitor according to an embodiment of the present invention with a configuration as shown in FIG. 2. The dispense volume monitor is receiving an input signal of voltage Vi from signal source 7 between nodes A and G1, respectively. Ri represents the output impedance of signal source 7, usually a relatively low value between 50Ω and 500Ω. Cs is the capacitance of cylindrical capacitor configuration 1 and represents the sensing capacitor. As shown below, the value of Cs is typically well below 1 pF. Cp and Re represent the input capacitance and input impedance of RF voltmeter 8, including the capacitance of the cable connecting cylindrical capacitor configuration 1 with RF voltmeter 8. The dispense volume monitor setup is generating an output signal of voltage Vo between nodes B and G2, respectively.

Figure 4:
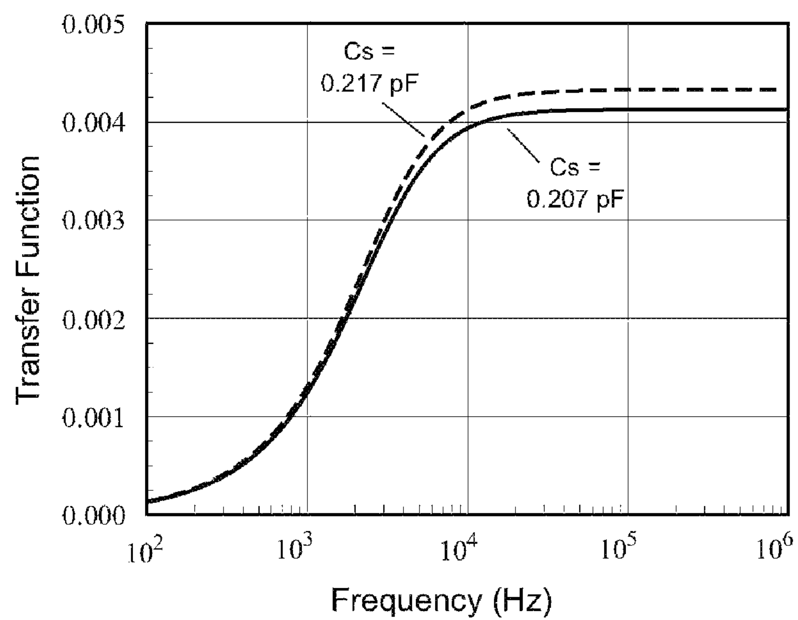
FIG. 4 shows a theoretical transfer function of the circuit diagram of FIG. 3.

FIG. 4 shows the theoretical transfer function T(f)=Vo/Vi of the circuit diagram according to FIG. 3 for capacitance values of 0.207 pF and 0.217 pF for Cs, respectively, assuming an input impedance of 1 MΩ for the RF voltmeter and a value Cp=50 pF for the RF voltmeter and connecting cable. It can be seen from the transfer function plots in FIG. 4, T(f) and, accordingly, the dispense volume sensor output signal Voltage Vo become independent of frequency f, but dependent on the value of Cs at frequencies above 10 kHz. This means frequency stabilization is not required when working at sufficiently high frequencies.

A cylindrical electrode configuration according an embodiment of the invention as shown in FIG. 1 can be described in electrical terms as four capacitive elements connected in series. The first capacitive element is represented by the air gap between upper electrode 5 and the surface of liquid sample 4. The second capacitive element is formed by the liquid sample 4, the volume of which has to be determined. The third capacitive element is formed by the cross section of the electrically non-conductive tray of the test plate 2 between the bottom of well 3 and the exterior bottom surface 11. A fourth and final capacitive element to be taken into account is formed, possibly, by a very small air gap between the bottom of test plate 2 and flat lower electrode 6.

Figure 5:
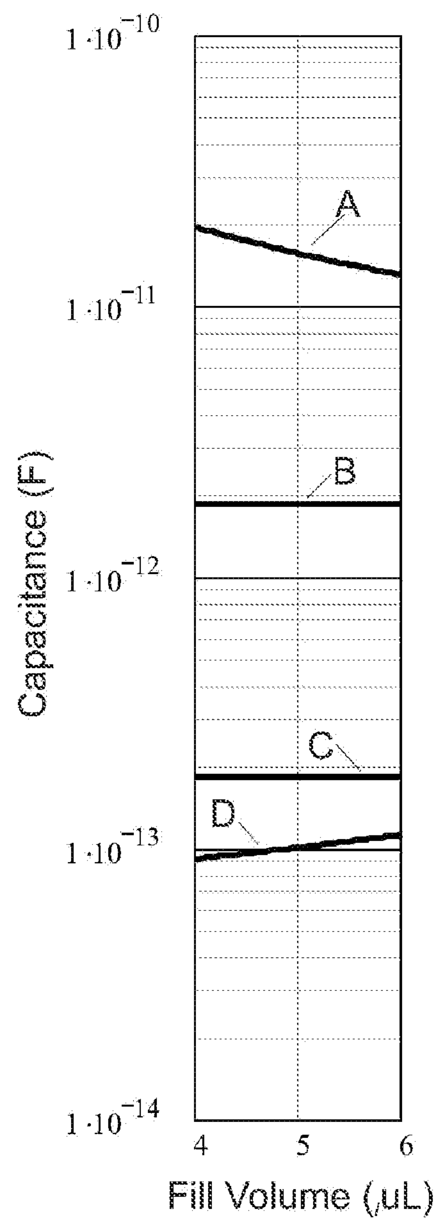
FIG. 5 shows a graph reflecting estimated capacitance values for the four capacitive elements of the cylindrical electrode configuration according to FIG. 1, in accordance with an embodiment of the invention.
Figure 6:
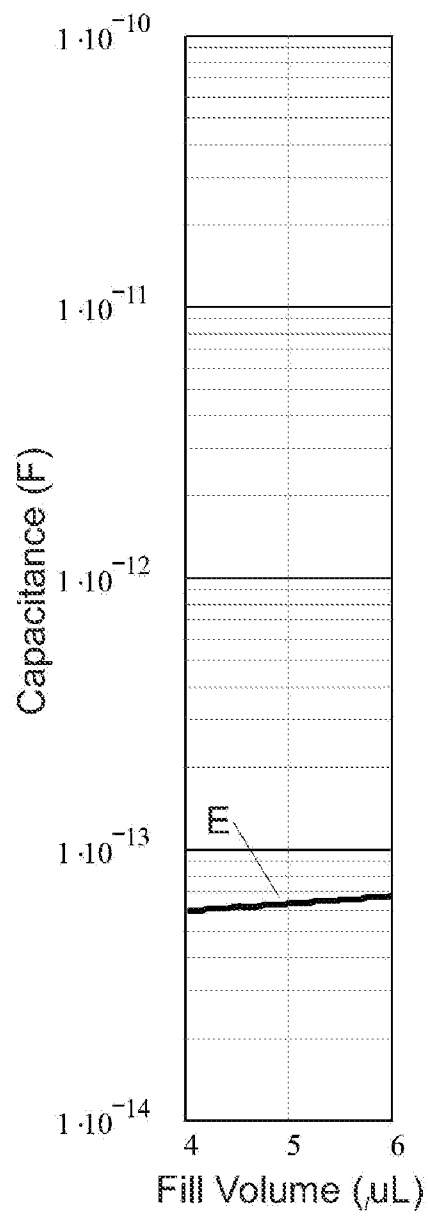
FIG. 6 shows a graph reflecting total capacitance (curve E) for the cylindrical electrode configuration as shown in FIG. 1, in accordance with an embodiment of the invention.

FIG. 5 shows estimated capacitance values for a cylindrical electrode configuration according to FIG. 1, whereby curve A represents the capacitance of the liquid sample, curve B represents the capacitance of a possible 50-μm air gap between the lower electrode and the lower outside of the test plate base, curve C is the capacitance of the test plate base, and curve D is the capacitance of the air space between the upper electrode and the surface of the dispensed liquid. All capacitance values are given for a dispensed liquid volume between 4 μL and 6 μL. FIG. 6 depicts the overall total capacitance (curve E) for a cylindrical electrode configuration according to FIG. 1, again for a dispensed liquid volume between 4 μL and 6 μL.

The total capacitance of capacitors, or capacitive elements, in series is always less than the capacitance of the smallest capacitor in the series. ($1/C_T=1/C_1+1/C_2+1/C_3+1/C_4$). In a series configuration, a larger capacitive element will have a smaller impact on the total capacitance $C_T$. This also becomes obvious from FIGS. 5 and 6, respectively, where the capacitance of the dispensed sample liquid (curve A) is the largest capacitive element. As can be seen, despite the fact that the capacitance curve A is decreasing with increasing sample dispense/fill volume, the total capacitance $C_T$ (curve E) is increasing with increasing sample dispense/fill volume. This increase can be explained because the average height, H, of the air gap becomes smaller with increasing sample dispense volume, and the capacitance of the air gap, $C_{air}$, is inversely proportional to the average height H according to the equation $C_{air}=\epsilon_o A/H$, where A is the effective area that is involved in forming the cylindrical capacitor configuration of FIG. 1.

Figure 7:
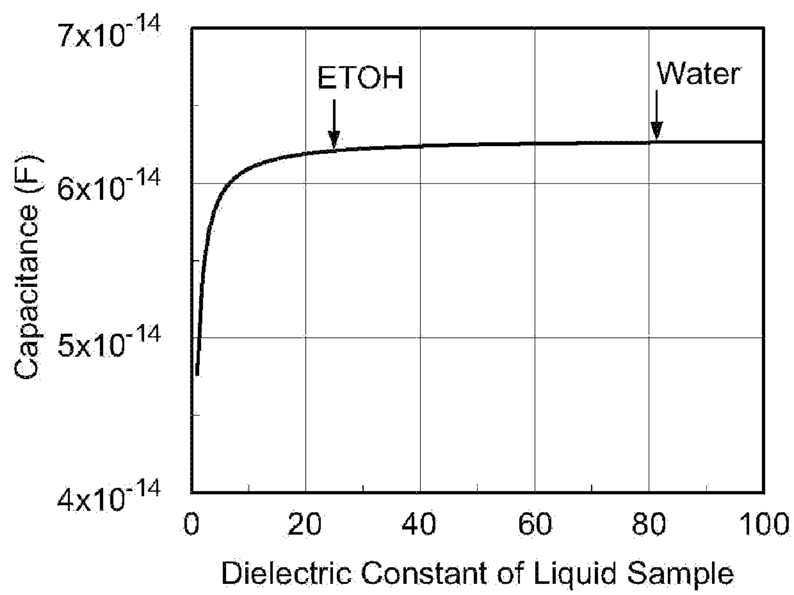
FIG. 7 shows a graph reflecting the total capacitance for a cylindrical electrode configuration according to FIG. 1, in accordance with an embodiment of the invention.

FIG. 7 shows the total capacitance for a cylindrical electrode configuration according to FIG. 1 for a dispensed liquid volume of 5 μL, whereby the dielectric constant of the liquid is varying between the values 1 and 100. The plot shown in FIG. 7 indicates that a dispense volume monitor per an embodiment of the present invention can be used to measure dispensed liquids with highly varying dielectric constants without a need for recalibration. This feature is a direct result of the relationship between the different capacitive element values shown in FIG. 5.

Figure 8:
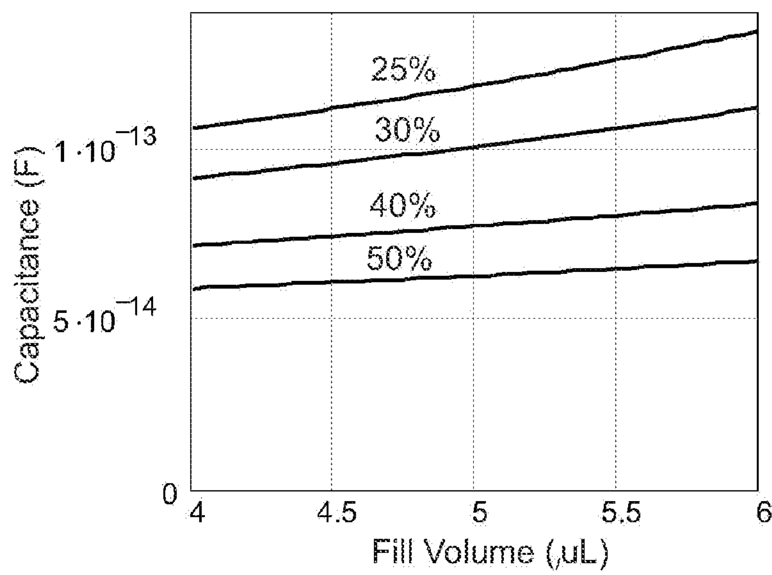
FIG. 8 shows a graph reflecting the total capacitance for a cylindrical electrode configuration according to FIG. 1, in accordance with an embodiment of the invention.

FIG. 8 shows the overall capacitance for a cylindrical electrode configuration according to FIG. 1, again for a dispensed/fill liquid volume between 4 μL and 6 μL, whereby the lower edge 30 of the upper electrode is positioned at 25%, 30%, 40% or 50% of the 2.8 mm total height of a well. As discussed previously, greater measurement sensitivity is achieved if the upper electrode is positioned deeper in the well.

Figure 9:
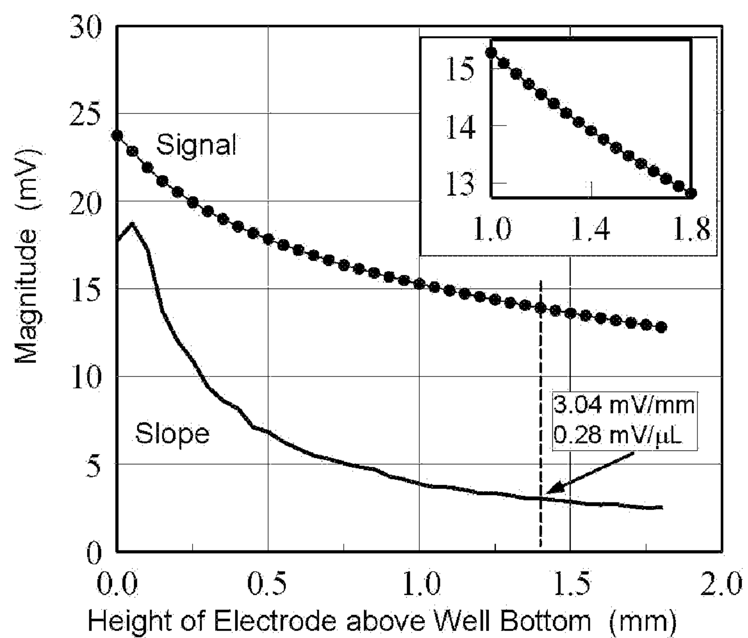
FIG. 9 shows a graph reflecting the voltage recorded using the electrical circuit shown in FIG. 2 on a cylindrical electrode configuration according to FIG. 1, in accordance with an embodiment of the invention.

FIG. 9 shows a recording of voltage from the electric circuit as shown in FIG. 2, using a cylindrical electrode configuration according to FIG. 1, as a function of the height of the upper electrode above the well bottom, with no liquids present in the well. The insert in the upper right corner of FIG. 9 shows that an excellent signal-to-noise ratio is achieved. Also shown is the slope of the voltage signal, which allows for a first estimate of the sensitivity for the dispense volume monitor. The estimated sensitivity is 0.28 mV/μL, if the upper electrode is positioned at 50% of the height of a 2.8 mm high well. From the absence of noise in the curve shown in FIG. 9, one can conclude that a dispense volume monitor according to an embodiment of the present invention will allow for fluid volume resolution well below 1 μL.

Figure 10:
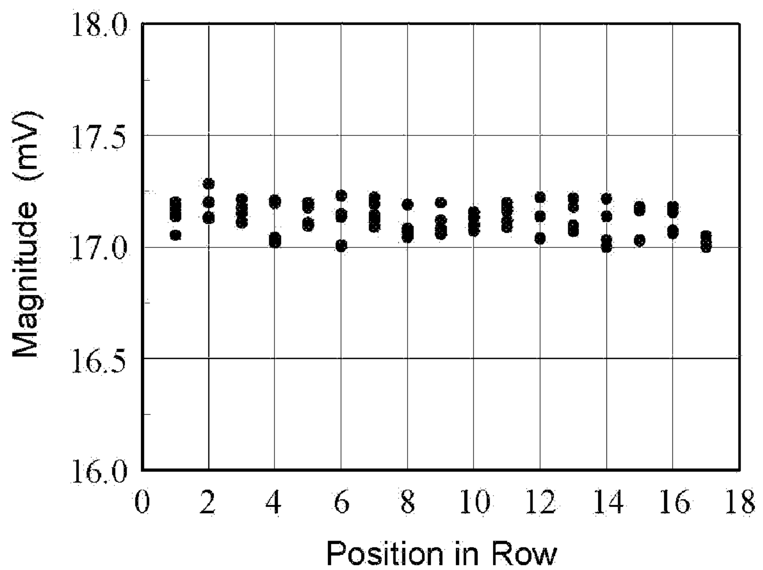
FIG. 10 shows a graph of recorded signals for open wells in a plastic test plate device, in accordance with an embodiment of the invention.

FIG. 10 shows recorded voltage signals for the each of the 136 wells in a plastic test plate comprising of open wells arranged in eight rows and seventeen columns with the upper electrode at a height position of 0.6 mm from the bottom of the well, which corresponds to 25% of the 2.8 mm well height. In this case, the wells had a diameter of 3.66 mm and no liquid reagents were present in the wells. The data given in FIG. 10 allows for an estimate of the maximum error in determining the dispensed volume in a whole two-dimensional array to be calculated. The mean magnitude for all 136 well voltage measurements in FIG. 10 is 17.1405 mV. The maximum deviations from the mean value are +0.18 mV and −0.14 mV, respectively. A sensitivity of 5.88 mV/mm or 0.54 mV/μL at a height of 0.6 mm, is then calculated using the sensitivity value from the slope of the curve in FIG. 9, which results in maximum errors from the mean dispensed liquid volume of +0.33 μL and −0.26 μL, respectively.

Figure 11:
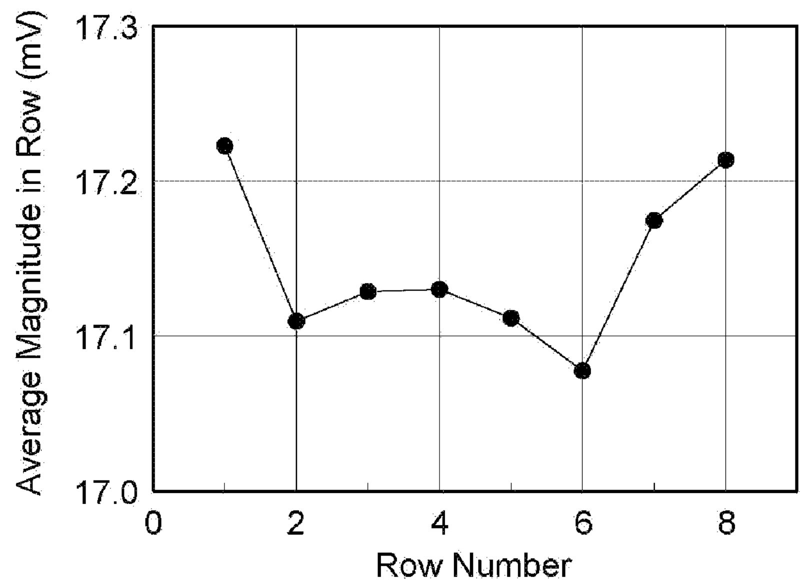
FIG. 11 shows a graph of the average signal magnitude for the eight rows in the measurement illustrated in FIG. 10, in accordance with an embodiment of the invention.

Molded plastic test plates typically show systematic geometric differences between rows that are located near the center and rows that are located closer to the edges. FIG. 11 depicts the average recorded voltage signal magnitude in each of the eight rows for the same measurement illustrated in FIG. 10. The maximum deviations in each row are +0.08 mV and −0.08 mV, respectively, which corresponds to a maximum measurement error in each row of only ±0.15 μL. Consequently, improved accuracy may be obtained with a dispense volume monitor according to an embodiment of the present invention by establishing a two-dimensional average magnitude array for the manufactured test plate part. This average magnitude array is typically the average value of the recorded voltage signals for each individual well after measuring a large sample of test plates. Thus if, for example, the voltage signals of 136 wells are measured for 100 test plates, a two-dimensional average magnitude array will be the average result from the 100 measurements for each of the 136 wells. In operation, the newly recorded magnitudes for each well would then be compared with the corresponding elements in the average magnitude array which were recorded earlier. Considering the maximum error of ±0.15 μL as determined above, a dispense volume monitor according to this embodiment of the present invention would allow for an accuracy of 3% for a target dispensed volume of 5 μL, in this instance.

Figure 12:
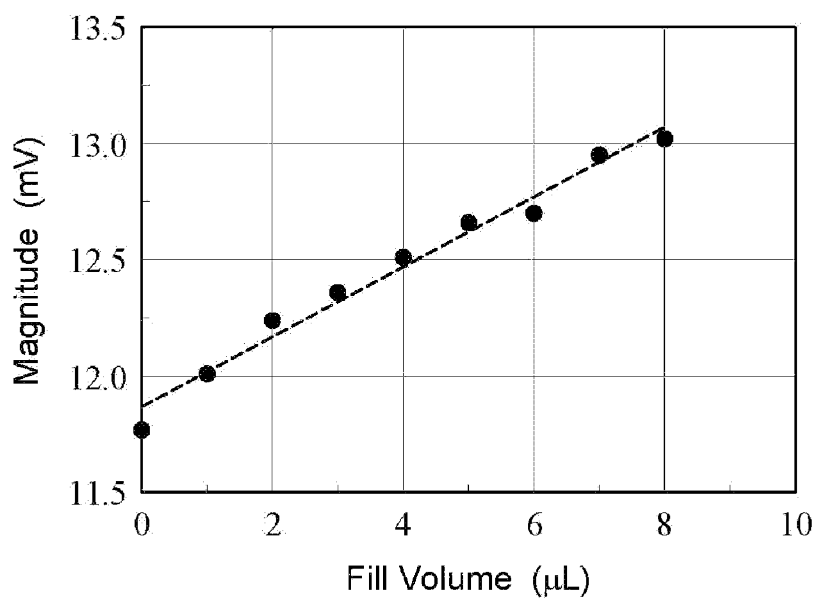
FIG. 12 shows a graph of the signal magnitudes recorded from the cylindrical electrode configuration according to FIG. 1, in accordance with an embodiment of the invention.

FIG. 12 shows initial measured signal magnitudes for a cylindrical electrode configuration according to FIG. 1, with the dispensed liquid volume varying between 0 and 8 μL. In this experiment, the wells in a plastic test plate were not exposed to corona treatment, which resulted in a highly irregular distribution of the dispensed liquid within the well. The liquid exhibited a highly nonsymmetrical distribution around the axis of the circular wells, in particular.

Figure 13:
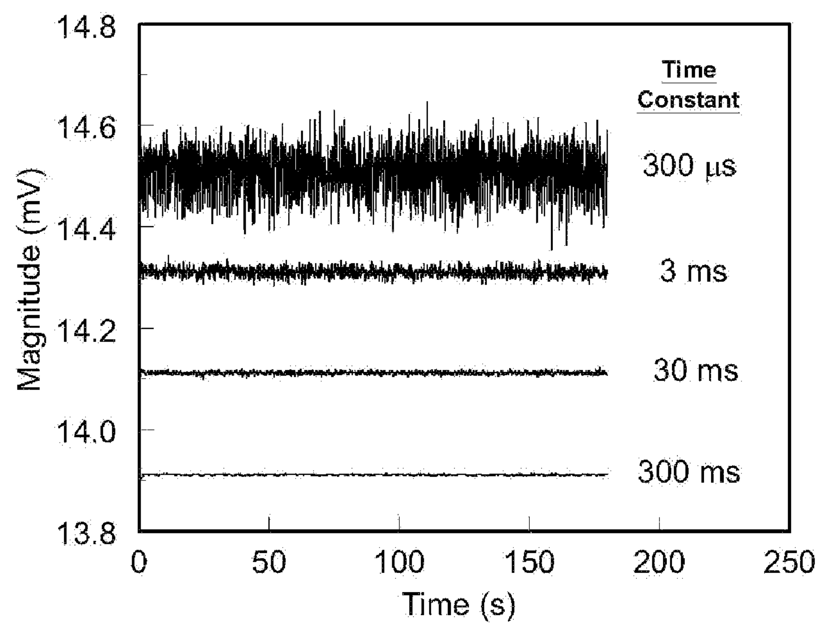
FIG. 13 shows a graph of recorded signals versus time, in accordance with an embodiment of the invention.

If liquid reagents are dispensed into two-dimensional open well arrays under production conditions, the time period available to monitor the volume dispensed into a single well is short. The effective capacitance values of a cylindrical capacitor configuration as illustrated in FIG. 1 are relatively small, typically lower than 1 pF. The electrical setup for a dispense volume monitor according to an embodiment of the invention, which is shown in FIG. 2, allows for determining such small capacitance values in about 1 ms, so that a whole test plate containing 136 wells could be monitored within, for example, one second. FIG. 13 shows recorded signal magnitudes versus time for a detection time constant that varies between 300 μs and 300 ms.

Figure 14:
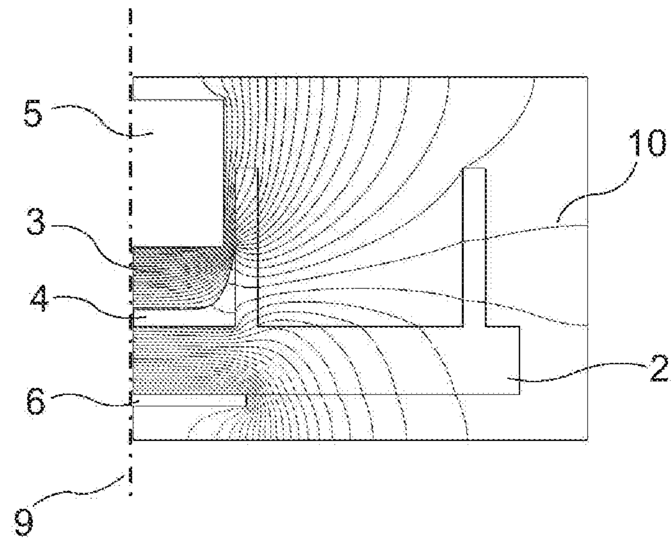
FIG. 14 are contour plots of the electric field distribution around the cylindrical electrode configuration according to FIG. 1, in accordance with an embodiment of the invention.

FIG. 14 depicts a contour plot of the electric field distribution around a cylindrical electrode configuration according to FIG. 1. The curves 10 in FIG. 14 represent lines of constant electrical potential. The well 3 in FIG. 14 has a height of 2.8 mm and a diameter of 3.66 mm. Upper electrode 5 is positioned at 50% of the well height and has a diameter of 3.2 mm. Lower flat electrode 6 has a diameter of 4 mm, and the base of test plate 2 has a thickness of 1.3 mm. Dispensed liquid reagent 4 is characterized by a strongly curved meniscus that has a pronounced impact on the electric field distribution inside and outside of the air gap between upper electrode 5 and liquid sample 4. The electric field distribution around symmetry axis 9 has been calculated using COMSOL's Multiphysics® V3.3 modeling program, sold by COMSOL, Inc., Burlington, Mass. Despite the fact that the model shown in FIG. 14 is a single cylindrical electrode configuration, in this instance, the calculated capacitance values differ with experimentally measured (using a plurality of electrodes in an array) capacitance values by only 12%.

Figure 15:
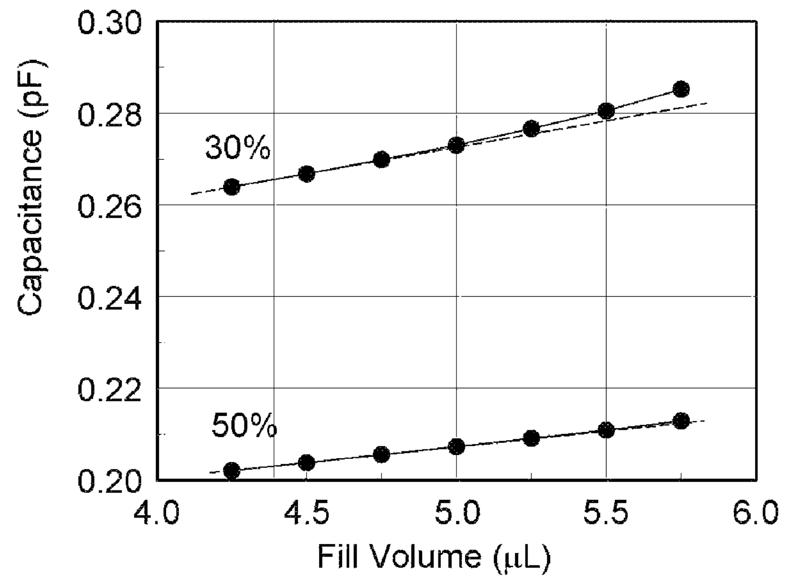
FIG. 15 shows a graph of estimated capacitance values versus dispensed liquid volume for upper electrode positions at various heights of a well according to FIG. 1, in accordance with an embodiment of the invention.
Figure 16:
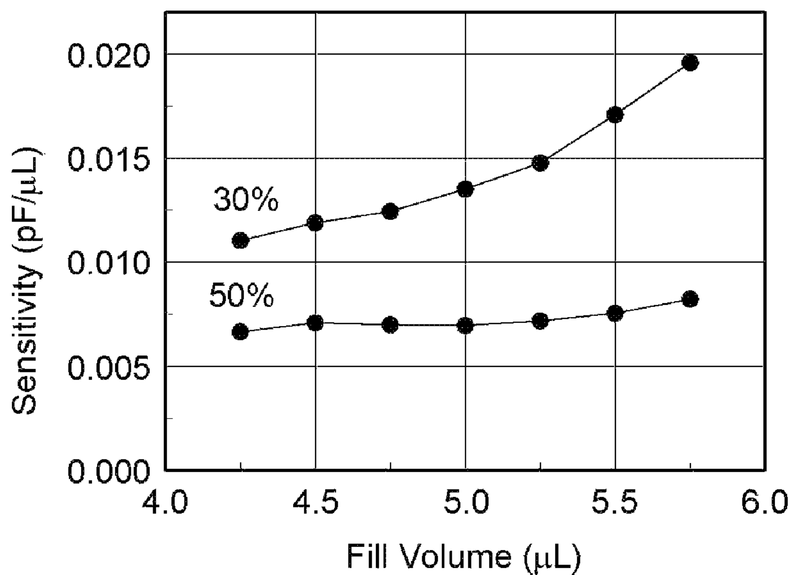
FIG. 16 shows a graph depicting the first derivative of the curves shown in FIG. 15, in accordance with an embodiment of the invention.
Figure 17:
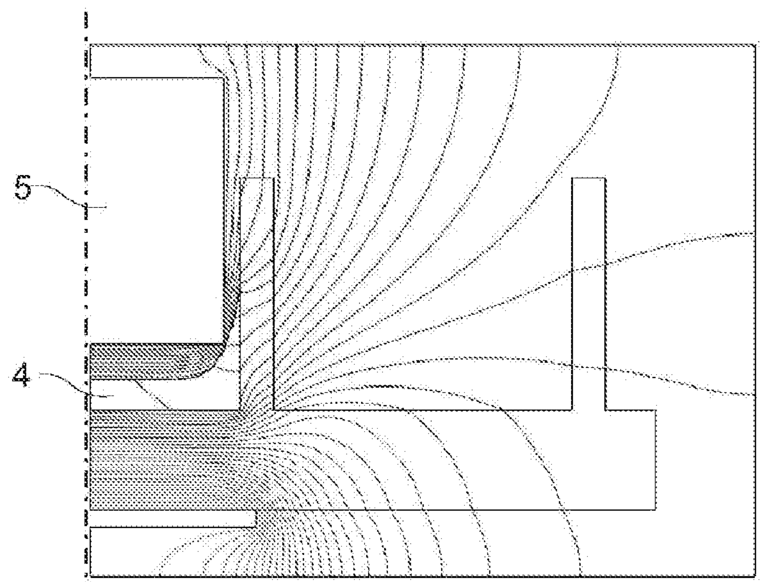
FIG. 17 are contour plots of the electric field distributed around a cylindrical electrode configured according to FIG. 1 for a relatively high dispensed liquid volume, in accordance with an embodiment of the invention.

FIG. 15 shows calculated capacitance values versus dispensed liquid volume for upper electrode positions at 30% and 50% of the 2.8 mm height of a well in a configuration as shown in FIG. 14. The estimate is based on electric field distributions as shown in FIG. 14. FIG. 16 depicts the first derivative of the curves in FIG. 15 that represent the sensitivity in pF/μL. The plots in FIGS. 15 and 16 indicate, as has been described above, that a lower position of upper electrode 5 results in increased sensitivity. These plots show also, however, that the system is approaching non-linear conditions for higher dispensed volumes, as indicated by the values plotted near 5.75 μL. FIG. 17 depicts a contour plot of the electric field distribution around a cylindrical electrode configuration per FIG. 14 for a relatively high dispensed liquid volume of 5.75 μL. As can be seen, the lines of constant electrical potential are extremely dense located near the edge of the upper electrode, and there is the possibility that the dispensed liquid reagent sample 4 may make direct contact with upper electrode 5.

Figure 18:
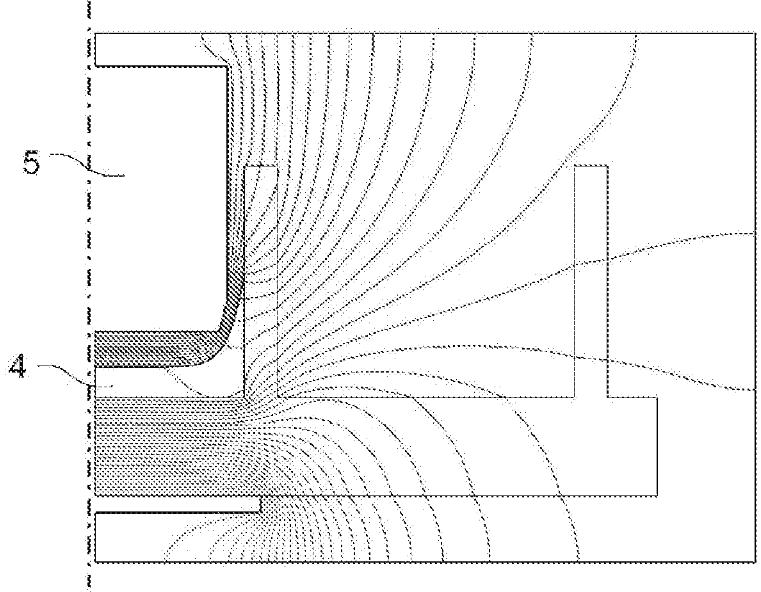
FIG. 18 are contour plots of the electric field distributed around a cylindrical electrode configuration where the upper electrode is beveled, using a relatively high dispensed volume, in accordance with an embodiment of the invention.
Figure 19:
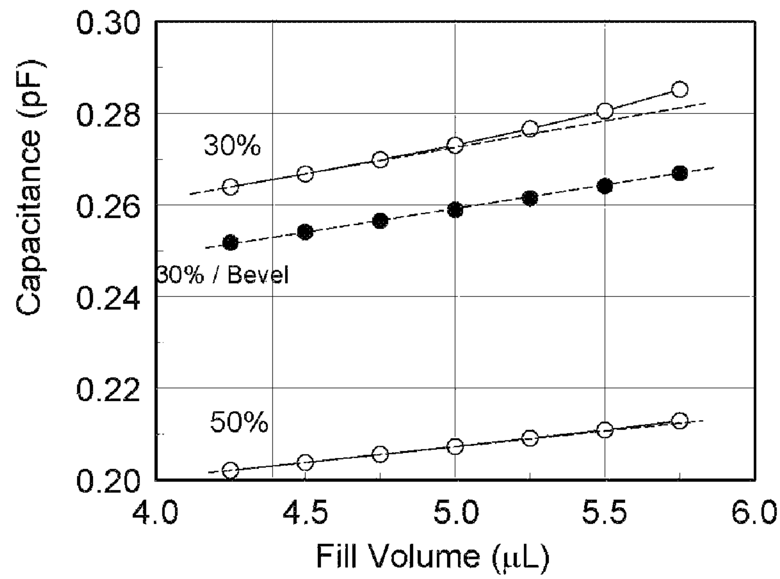
FIG. 19 shows a graph of the estimated capacitance values versus dispensed volume for a beveled upper electrode as depicted in FIG. 18, when positioned at various heights of a well against the upper electrode as depicted in FIG. 1, in accordance with an embodiment of the invention.
Figure 20:
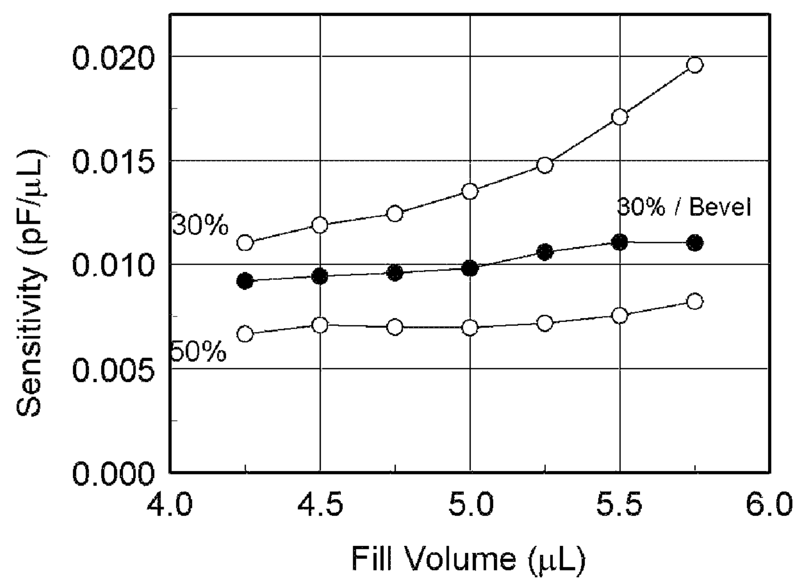
FIG. 20 shows a graph depicting the first derivative of the estimated capacitance values versus dispensed liquid volume for a beveled upper electrode depicted in FIG. 18, against the upper electrode as depicted in FIG. 1, in accordance with an embodiment of the invention.

FIG. 18 shows a contour plot of the electric field distribution around a cylindrical electrode configuration of an embodiment of the present invention where the upper electrode 11 is beveled in its lower section, again for a relatively high dispensed liquid volume of 5.75 μL. As shown, the lines of constant electrical potential are somewhat less dense near the lower section of the upper electrode, and the minimum distance between liquid sample 4 and upper electrode 11 is significantly larger compared to the case illustrated in FIG. 17. This results in reduced possibility of direct contact between the liquid and the upper electrode. The effect of using a beveled lower section in upper electrode 11 is illustrated in FIGS. 19 and 20. FIG. 19 shows the same curves as shown in FIG. 15, but also shows estimated capacitance values versus dispensed liquid volume for a beveled upper electrode as shown in FIG. 18, positioned at 30% of the 2.8 mm height of a well as shown in FIG. 1. The presence of a bevel results in a somewhat lower capacitance value, but also reduces the nonlinear behavior of the capacitance-versus-volume curve. The sensitivity is also somewhat lower for the beveled upper electrode.

Figure 21:
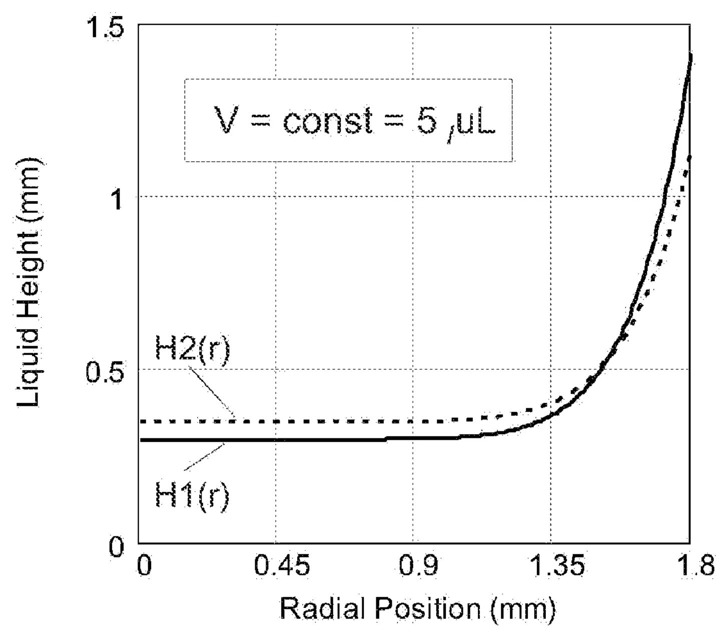
FIG. 21 shows a graph of liquid height versus well radial position to depict two different meniscus shapes for a dispensed liquid volume in an open well according to FIG. 18, in accordance with an embodiment of the invention.
Figure 22:
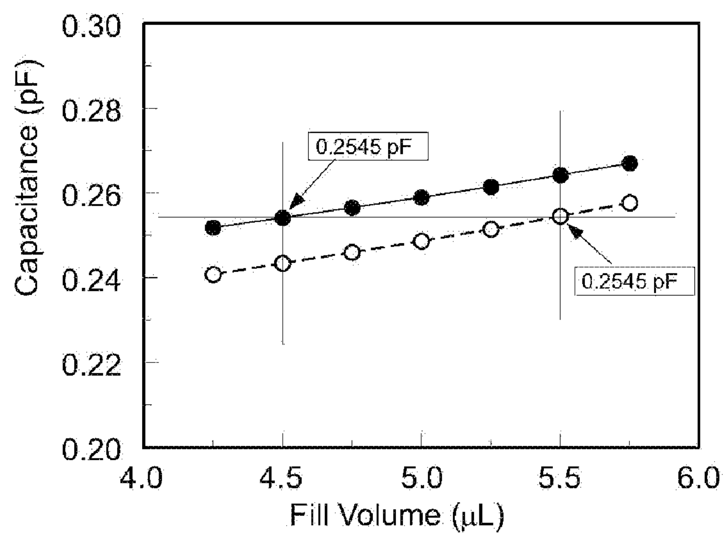
FIG. 22 shows a graph of estimated capacitance values versus dispensed liquid volume for a beveled upper electrode according to FIG. 18 in accordance with an embodiment of the invention.
Figure 23:
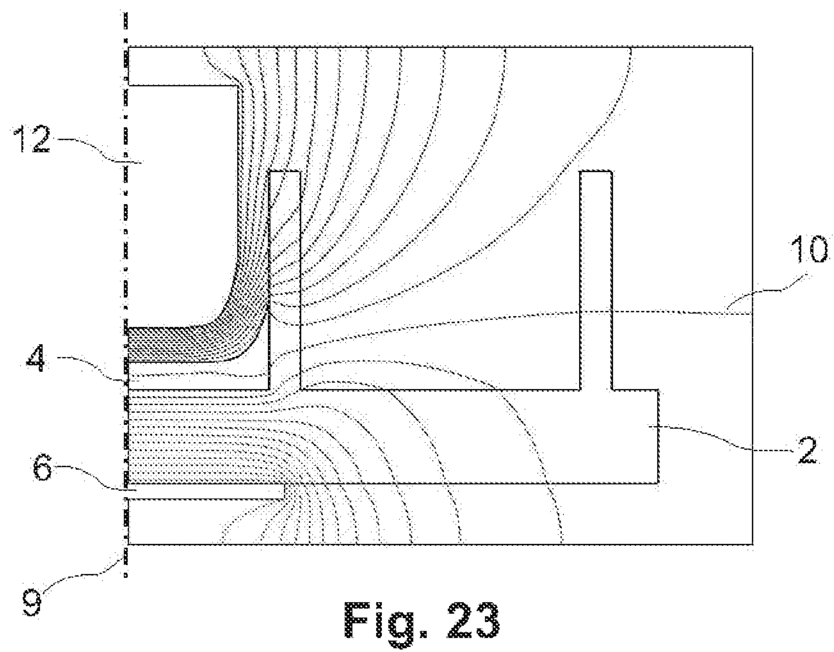
FIG. 23 shows contour plots of the electric field distribution around a cylindrical electrode configuration for a relatively high liquid dispense volume, in accordance with an embodiment of the invention.

FIG. 21 illustrates two different meniscus shapes for a constant dispensed volume of 5 μL in a well according to FIG. 18 with a height of 2.8 mm and an inner diameter of 3.66 mm. FIG. 22 shows estimated capacitance values versus dispensed liquid volume for a beveled upper electrode positioned at 30% of the 2.8 mm height of a well as shown in FIG. 18. The estimate is based on electric field distributions as shown in FIG. 18. The upper curve in FIG. 22 corresponds to the meniscus profile H1(*r*) in FIG. 21, and the lower curve in FIG. 22 corresponds to the meniscus profile H2(*r*) in FIG. 21. In the case of varying dispensed liquid volumes, profiles H1(*r*) and H2(*r*) are shifted up and down, but keep their shape constant. The two plots in FIG. 22 show that a change in the meniscus shape can have a negative impact on the accuracy of a dispense volume monitor. If, for instance, the capacitance value is determined to be 0.2545 pF, this value could be produced by a dispensed liquid volume of 4.5 μL, if the meniscus shape matches the solid line curve H1(*r*) in FIG. 21. The very same capacitance value, however, could also be caused by a dispensed liquid volume of 5.5 μL, if the meniscus shape matches the dashed curve H2(*r*) in FIG. 21. It has been found by the inventors that this problem can be greatly reduced by using an upper electrode of a smaller diameter and by designing the upper electrode in such a way that the lower profile section of the upper electrode resembles the shape of an average meniscus for the liquids dispensed. FIG. 23 depicts a contour plot of the electric field distributed around a cylindrical electrode configuration of an embodiment of the present invention for a relatively high dispensed volume of 5.75 μL, whereby the upper electrode has a smaller diameter and the lower profile section of the upper electrode resembles the shape of an average meniscus.

Figure 24:
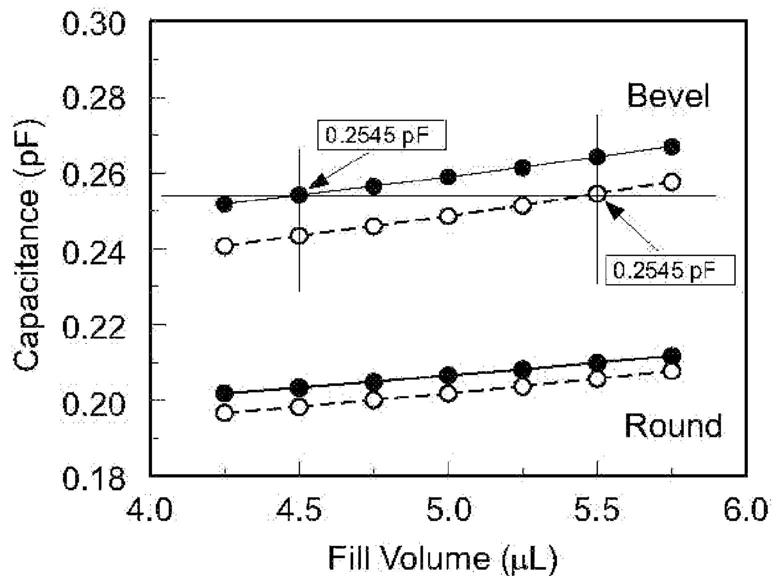
FIG. 24 shows a graph of the estimated capacitance values versus dispense volume for a beveled upper electrode as shown in FIG. 18, against, an upper round electrode as shown in FIG. 23, in accordance with an embodiment of the invention.

FIG. 24 corresponds to FIG. 22, but additionally shows estimated capacitance values versus dispensed volume for upper electrode 12 according to FIG. 23 with a smaller diameter and a lower profile section resembling the shape of an average meniscus for the liquids to be dispensed. Here, the two capacitance-versus-volume curves for meniscus profiles H1(*r*) and H2(*r*), respectively, are located much closer together, and the problem discussed in connection with the plots in FIG. 22 is significantly reduced.

Figure 25:
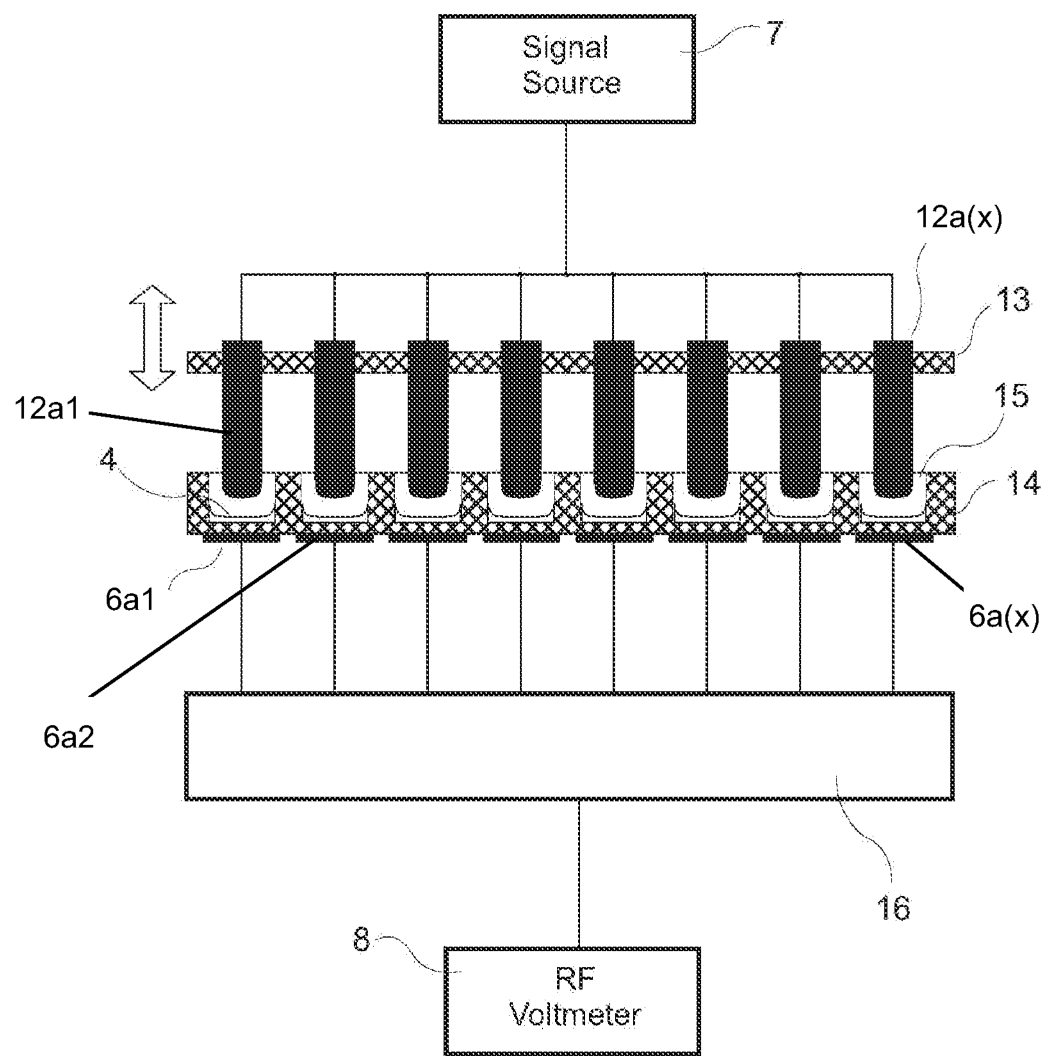
FIG. 25 shows a dispense volume monitor comprising of a multiplexed electrode arrangement for the interrogation of two-dimensional arrays of wells, in accordance with an embodiment of the invention.

FIG. 25 is an illustration depicting a dispense volume monitor according an embodiment of the present invention, comprising a multiplexed arrangement for the interrogation of two-dimensional well arrays. A multiplexer or mux (occasionally the term muldex is also found, for a combination multiplexer-demultiplexer) is a device that performs multiplexing; it selects one of many analog or digital input signals and outputs that signal into a single line. A signal source 7 is connected in parallel with all upper electrodes $\mathbf{12}a_{(x)}$ of the array (where x is equal to the total number of wells in the array). Upper electrodes $\mathbf{12}a_{(x)}$ are mechanically supported and held in place by electrically insulating member 13. Lower flat electrodes $\mathbf{6}a_{(x)}$ (where x is equal to the total number of wells in the array) are arranged in a matching array below electrically insulating test plate 14 containing the two-dimensional well array 15. All flat lower electrodes $\mathbf{6}a_{(x)}$ are connected to the inputs of multiplexer 16, which has relatively low input impedance values allowing for fast switching between measurement channels. The output of multiplexer 16 is connected to the input of RF voltmeter 8. A multiplexer therefore can be considered as a multiple-input, single-output switch, and a demultiplexer as a single-input, multiple-output switch. To perform a measurement on all wells in array 15, member 13 is lowered until upper electrodes $\mathbf{12}a_{(x)}$ are positioned at the desired height inside well array 15. A common computer (not shown) is used to control multiplexer 16 so that the lower electrodes $\mathbf{6}a_{(x)}$ are scanned serially. The recorded signal magnitudes are used to calculate the dispensed liquid volume in each well of the array.

In another embodiment of the present invention, the accuracy of a dispense volume monitor can be improved further by establishing a two-dimensional average magnitude array for a manufactured test plate type without dispensed liquids. In operation, the magnitudes recorded after liquid is dispensed into the wells would then be compared with the corresponding elements in the average magnitude array that has been recorded earlier for this type of test plate.

In an additional embodiment of the present invention, the accuracy of a dispense volume monitor could be improved even further by using the signal magnitudes for each well of a test plate (in place of an average signal magnitude for the test plate) before and after the dispensing of liquid reagents, and using both recorded values for the calculation of the dispensed liquid volume in each well. In this case, irregularities in a molded test plate product could be cancelled out when calculating the dispensed liquid volume. This additional embodiment would comprise the following steps of providing an electrically insulating test plate comprising a two-dimensional array of open wells, coaxially inserting a cylindrical upper electrode, having a diameter that is smaller than the well diameter and having an optimized lower profile, into each well, positioning the upper electrode at a defined position above the well bottom, determining a reference capacitance value of the capacitor formed by the upper electrode in each well and a lower flat electrode arranged adjacent to the lower outside of the test plate below each well, removing the upper electrode in each well, dispensing a target volume of a liquid reagent into each well, coaxially inserting the cylindrical upper electrode, having a diameter that is smaller than the well diameter and having an optimized lower profile, into each well, positioning the upper electrode at the same defined position above the well bottom as used for the reference capacitance reading, determining a second capacitance value of the capacitor formed by the upper electrode in each well and a lower flat electrode arranged adjacent to the lower outside of the test plate below each well, determining a liquid-volume-related capacitance value for each well by subtracting said reference capacitance value from said second capacitance value in each well, and determining the actual dispensed liquid reagent volume in each individual well by comparing the liquid-volume-related capacitance value in each well with liquid-volume-related calibration capacitance values determined earlier for known dispensed liquid reagent volumes.

It should be noted that the first part of the procedure of the above-described additional embodiment could also be used advantageously for performing quality control measurements in connection with the production of plastic test plates that contain two-dimensional arrays of open wells. If the reference capacity values within an array of wells are all the same, the molding process can be considered perfect. If the reference capacity values exhibit variations, the molding process has to be considered as imperfect, or the array of wells may contain impurities not suitable for the intended use of the device. For this application of the additional embodiment of the present invention, the upper electrode should be positioned preferably at approximately 30% to 50% of the well height.

Figure 26:
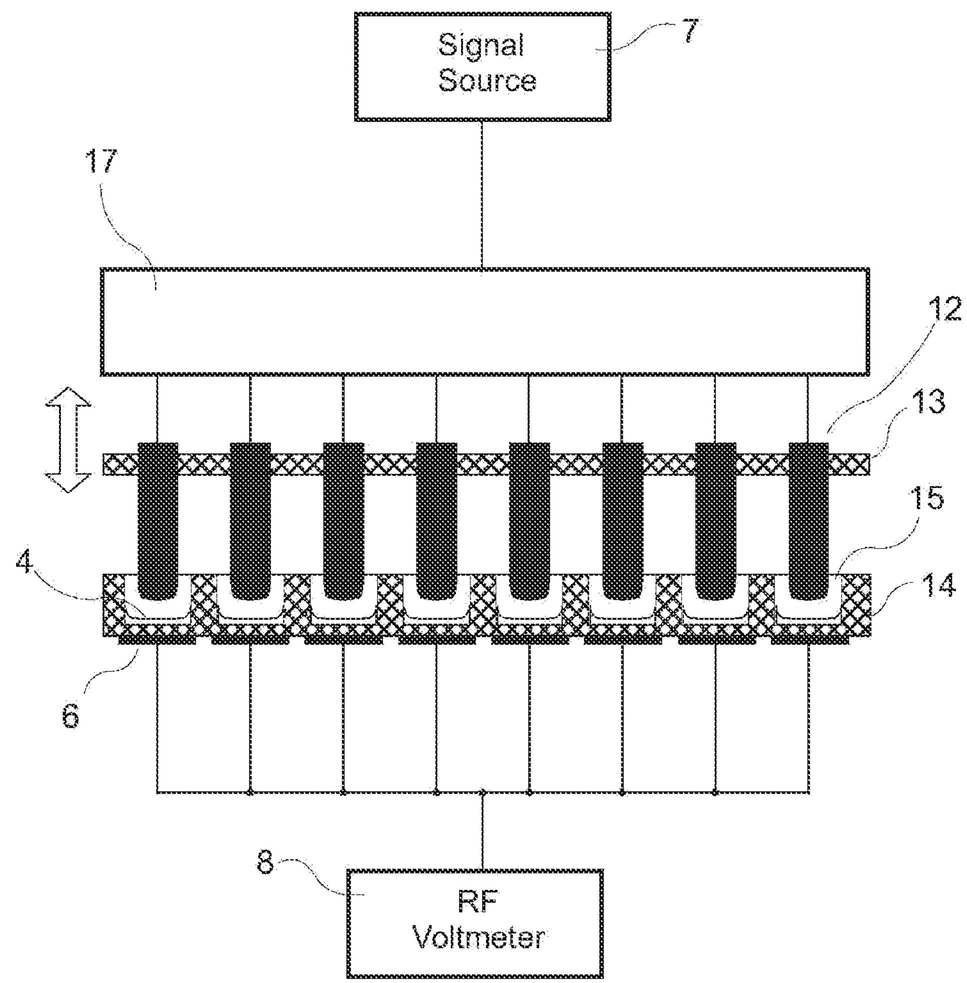
FIG. 26 shows an embodiment of the multiplexed dispense volume monitor, similar to the arrangement shown in FIG. 25, but with the upper electrodes electrically activated serially, and all the flat lower electrodes connected in parallel with an RF voltmeter.

FIG. 26 shows a dispense volume monitor according to another embodiment of the present invention, which is similar to the arrangement shown in FIG. 25, but with upper electrodes 12 electrically activated serially by computer-controlled (computer not shown) demultiplexer 17, which has relatively low output impedance values allowing fast switching between the channels. All lower flat electrodes 6 are configured in parallel and connected to the input of RF voltmeter 8. The additional advantage of this configuration over the setup shown in FIG. 25 is demultiplexer 17 can have extremely low output impedance values of 50Ω or even less, which allows for extremely fast operation without an extremely small transfer function. In accordance with an aspect of the configuration of FIG. 26, only one upper electrode 12 would be electrically active at any given time, and only one lower electrode 6 would receive an RF electric field. All other lower electrodes would face an in-active upper electrode at constant electrical ground potential. Therefore, all other lower electrodes would act as one capacitor Cp' in parallel with capacitor Cp in the circuit diagram shown in FIG. 3. If, e.g., the array has 136 wells or elements in the form of a cylindrical capacitor configuration of 0.20 pF per well (see FIG. 24), then the 135 other cylindrical capacitor configurations would represent a capacitor Cp'=135*0.20 pF=27 pF. Compared to the setup in FIG. 25, the transfer function in the plateau region of a setup according to FIG. 26 would decrease by 35%, taking the original value Cp=50 pF into account.

Figure 27:
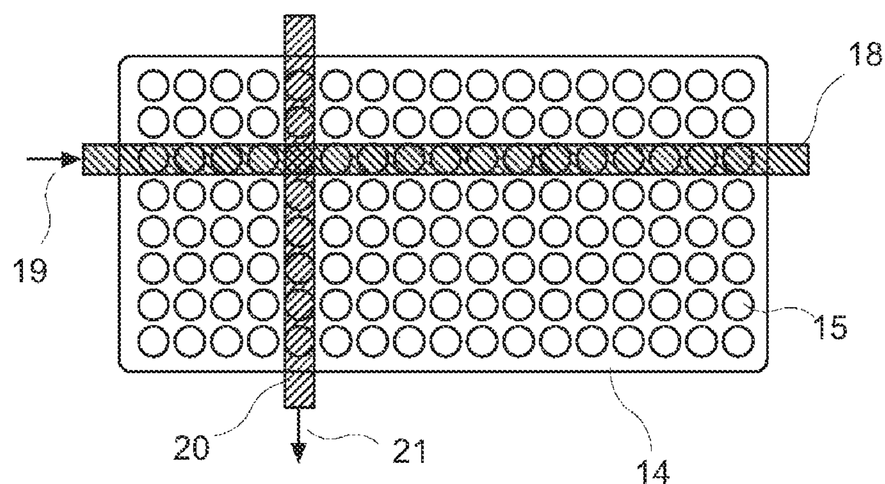
FIG. 27 illustrates a sequence of operation of the dispense volume monitor in accordance with an embodiment of the invention.

The multiplexed sensor arrangements as shown in FIGS. 25 and 26 utilize multiplexers with a channel quantity identical to the number of upper or lower electrodes. Multiplexers of reduced channel quantities can be used with a sensor arrangement that is illustrated symbolically in FIG. 27. Here, it is assumed that a multi-well plate has 136 wells or elements, arranged in a matrix of seventeen columns and eight rows. A demultiplexer with only eight output channels is used to excite one whole row of upper electrodes at a time, as indicated in FIG. 27 by incoming arrow 19 and band 18. The simultaneous excitation of all upper electrodes in a row is achieved by connecting them in parallel electrically. A multiplexer with seventeen input channels is used on the detection side to connect all lower flat electrodes in one column with the input of the RF voltmeter, as indicated in FIG. 27 by outgoing arrow 21 and band 20. All lower electrodes in a column are made available to the input of the multiplexer by connecting them in parallel electrically. At any given time, only one lower electrode in a column will receive an RF field, while the remaining seven electrodes represent a parallel capacitance of value Cp"=7*0.20 pF=1.4 pF. In operation, a row 18 would be scanned through all columns from left to right. This action results in the read-out of that row. The next row would then be scanned again through all columns from left to right, which results in the read-out of the next row, and so on until the whole array has been read.

Figure 28:
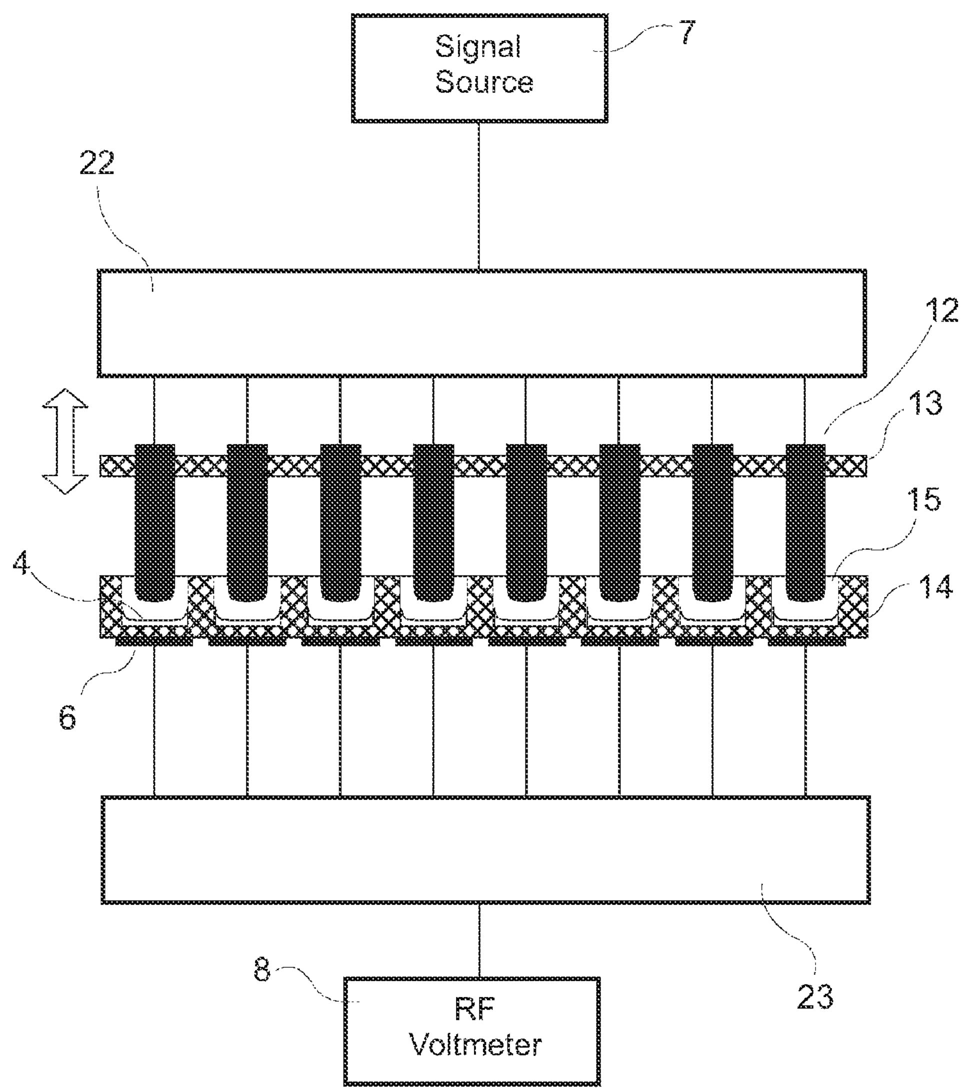
FIG. 28 shows a dispense volume monitor comprising a multiplexed/demultiplexed electrode arrangement for the interrogation of two-dimensional arrays of wells, in accordance with an embodiment of the invention.

FIG. 28 depicts a corresponding multiplexed sensor arrangement according to the embodiment described in FIG. 27, showing a demultiplexer 22 and a multiplexer 23. The lower electrodes 6 are insulated from each other and connected with the inputs of multiplexer 23. Both demultiplexer 22 and multiplexer 23 are controlled and synchronized by a common computer, which is not shown. The setup of FIG. 28 has the advantages over the configurations depicted in FIGS. 25 and 26 in that for example demultiplexers and multiplexers of a significantly lower number of channels can be used.

Figure 30:
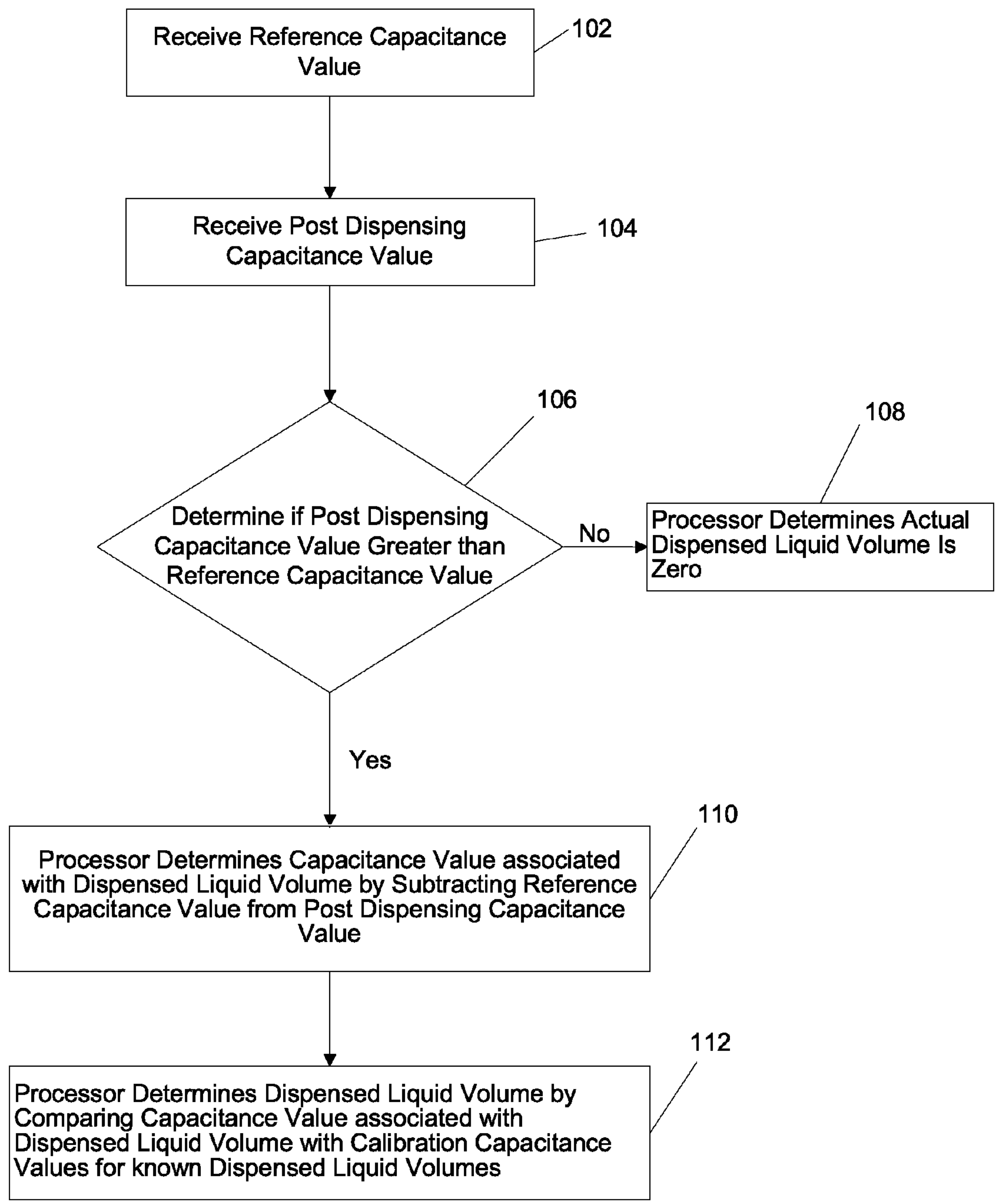
FIG. 30 illustrates a flowchart depicting a sequence of operation of a processor, in accordance with an embodiment of the invention.

FIG. 30 shows a sequence of operation of a processor 200 in accordance with an embodiment of the invention. The reference capacitance value is received by the processor 200 (step 102). This predetermined valued would be accessed by processor 200 from memory or storage device (not shown). The post dispensing capacitance value is then received by the processor 200 from cylinder capacitor arrangement 1 (step 104) after the liquid has been dispensed. The processor 200 then determines if the post dispensing capacitance value is greater than the reference capacitance value (step 106). If the post dispensing capacitance value is equal to the reference capacitance value, the processor 200 then determines that the actual dispensed volume of liquid is zero (step 108). However, if the post dispensing capacitance value is greater than the reference capacitance value, the processor 200 then calculates the capacitance value of the dispensed volume of liquid, for example, subtracting the reference capacitance value from the post dispensing capacitance value (step 110). The processor 200 then determines the dispensed liquid volume by comparing the capacitance value associated with dispensed liquid volume with calibration capacitance values for known dispensed liquid volumes (step 112).

Modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A dispense volume monitor comprising:
a capacitor that comprises:
a first electrode;
a second electrode; and
a test plate comprising at least one well;
wherein said first electrode is cylindrical, having a first end and a second end and an outer diameter that is smaller than an inner diameter of said at least one well;
wherein said first electrode is capable of being positioned at 50% or less of the total height of said at least one well of said test plate and said second electrode is adjacent to an exterior bottom surface of said test plate, below said at least one well.

2. The dispense volume monitor of claim 1, wherein said second end of said first electrode is positioned at 30% or less of the total height of said at least one well.

3. The dispense volume monitor of claim 1, wherein said second end of said first electrode has the shape of an average meniscus of a liquid volume in said at least one well.

4. The dispense volume monitor of claim 1, wherein said test plate is made from electrically non-conductive materials.

5. The dispense volume monitor of claim 1, further comprising a processor configured for:
measuring capacitance of said capacitor, and
determining a volume of a dispensed liquid in said well by comparing said measured capacitance value with a reference capacitance value.

6. The dispense volume monitor of claim 5, wherein the measured capacitance of said capacitor is substantially independent of the dielectric constant of a material that is present in said well.

7. A dispense volume monitor comprising:

a capacitor that comprises:

a first electrode;

a second electrode; and a test plate comprising at least one well;

wherein said first electrode is cylindrical, having a first end and a second end and an outer diameter that is 80% or less of said inner diameter of said at least one well; and wherein said first electrode is capable of being positioned in said at least one well of said test plate and said second electrode is adjacent to an exterior bottom surface of said test plate, below said at least one well.

8. The dispense volume monitor of claim 7, wherein said first electrode outer diameter is 60% or less of said inner diameter of said at least one well.

9. A dispense volume monitor comprising:

a plurality of upper electrodes arranged in an array of at least one row and at least one column held in place by a first electrical insulating member;

a plurality of lower electrodes arranged in a matching array of at least one row and at least one column;

a test plate comprising a plurality of wells arranged in a matching array of at least one row and at least one column;

wherein said plurality of lower electrodes are adjacent to an exterior bottom surface of said test plate, below said plurality of wells, such that on insertion of said plurality of upper electrodes into said plurality of wells a plurality of capacitors are formed; and a multiplexer having a plurality of input channels and one output channel, wherein said plurality of lower electrodes are connected to said plurality of input channels of said multiplexer and isolated from each other and individually connected with one of said plurality of inputs of said multiplexer, and said one output channel is connected to an input of a voltmeter.

10. The dispense volume monitor of claim 9, further comprising a signal source connected in parallel with each of said plurality of upper electrodes.

11. A dispense volume monitor comprising:

a plurality of upper electrodes arranged in an array of at least one row and at least one column held in place by a first electrical insulating member;

a plurality of lower electrodes arranged in a matching array of at least one row and at least one column;

a test plate comprising a plurality of wells arranged in a matching array of at least one row and at least one column;

wherein said plurality of lower electrodes are adjacent to an exterior bottom surface of said test plate, below said plurality of wells, such that on insertion of said plurality of upper electrodes into said plurality of wells a plurality of capacitors are formed;

a multiplexer having a plurality of input channels and one output channel, wherein said plurality of lower electrodes are connected to said plurality of input channels of said multiplexer, and said one output channel is connected to an input of a voltmeter;

wherein said plurality of lower electrodes are connected with each other, and connected with said input of said voltmeter.

12. A dispense volume monitor comprising:

a plurality of upper electrodes arranged in an array of at least one row and at least one column held in place by a first electrical insulating member;

a plurality of lower electrodes arranged in a matching array of at least one row and at least one column;

a test plate comprising a plurality of wells arranged in a matching array of at least one row and at least one column;

wherein said plurality of lower electrodes are adjacent to an exterior bottom surface of said test plate, below said plurality of wells, such that on insertion of said plurality of upper electrodes into said plurality of wells a plurality of capacitors are formed; and a demultiplexer having one input channel and a plurality of output channels, wherein said one input channel is connected to an output of a signal source and said plurality of upper electrodes are connected to the said plurality of output channels of said demultiplexer;

wherein said demultiplexer comprises a plurality of output channels equal to the number of upper electrodes in one row of said array of upper electrodes.

13. The dispense volume monitor of claim 12, wherein said demultiplexer comprises a plurality of output channels equal to the number of upper electrodes in said array of upper electrodes.

14. The dispense volume monitor of claim 12, wherein said plurality of upper electrodes are electrically activated in a series mode by said demultiplexer.

15. A dispense volume monitor comprising:

a plurality of upper electrodes arranged in an array of at least one row and at least one column held in place by a first electrical insulating member;

a plurality of lower electrodes arranged in a matching array of at least one row and at least one column; and a test plate comprising a plurality of wells arranged in a matching array of at least one row and at least one column;

wherein said plurality of lower electrodes are adjacent to an exterior bottom surface of said test plate, below said plurality of wells, such that on insertion of said plurality of upper electrodes into said plurality of wells a plurality of capacitors are formed;

a demultiplexer having one input and a plurality of outputs, wherein said input of said demultiplexer is connected to an output of a signal source and said plurality of upper electrodes are connected to the said plurality of outputs of said demultiplexer; and a multiplexer having a plurality of inputs and one output, wherein said plurality of lower electrodes are connected to said plurality of inputs of said multiplexer, and said output of said multiplexer connected to an input of a voltmeter;

wherein said demultiplexer comprises a plurality of outputs equal to the number of dispense needles in one row of an array of dispense needles.

16. The dispense volumn monitor of claim 15, wherein said upper electrodes are electrically activated in a series mode by said demultiplexer.

17. A dispense volume monitor comprising:

a plurality of upper electrodes arranged in an array of at least one row and at least one column held in place by a first electrical insulating member;

a plurality of lower electrodes arranged in a matching array of at least one row and at least one column;

a test plate comprising a plurality of wells arranged in a matching array of at least one row and at least one column; wherein said plurality of lower electrodes are adjacent to an exterior bottom surface of said test plate, below said plurality of wells, such that on insertion of said plurality of upper electrodes into said plurality of wells a plurality of capacitors are formed;

a demultiplexer having one input and a plurality of outputs, wherein said input of said demultiplexer is connected to an output of a signal source and said plurality of upper electrodes are connected to the said plurality of outputs of said demultiplexer; and a multiplexer having a plurality of inputs and one output, wherein said plurality of lower electrodes are connected to said plurality of inputs of said multiplexer, and said output of said multiplexer connected to an input of a voltmeter;

wherein said multiplexer comprises a plurality of inputs equal to the number of receiving cylinders in one column of an array of dispense needles.

18. A method to determine a volume of dispensed liquid comprising:

inserting a first electrode into a container, wherein said container comprises a dispensed liquid sample volume, and wherein a second electrode is arranged adjacent to the lower outside of said container, thereby forming a capacitor, measuring the capacitance of said capacitor, determining the capacitance value of said dispensed liquid sample volume, and determining the volume of said dispensed liquid sample by comparing said capacitance value of said dispensed liquid sample volume with a calibration capacitance value;

wherein said capacitance value of said dispensed liquid sample volume is calculated by subtracting a reference capacitance value from said measured capacitance value.

19. The method of claim 18, wherein said reference capacitance value is the capacitance value of said capacitor with no liquid sample present in said container.

20. The method of claim 19, wherein a greater said measured capacitance value when compared to said reference capacitance value indicates the presence a volume of said dispensed liquid.

21. The method of claim 19, wherein a processor is used to calculate said capacitance value of said dispensed liquid sample volume.

22. The method of claim 18, wherein a processor is used to calculate the volume of said dispensed liquid.

23. The method of claim 18, wherein said calibration capacitance value is a capacitance value for a known dispensed liquid sample volume.

24. The method of claim 18, wherein said measured capacitance value is substantially independent of the dielectric constant of said liquid sample.

25. The method of claim 18 wherein said capacitor is a cylinder shaped parallel plate capacitor.

26. The method of claim 18, wherein said comparison of said capacitance value of said dispensed liquid sample volume with a calibration capacitance value is carried out by a processor.

27. A method to determine a volume of dispensed liquid comprising:

inserting a first electrode into a container, wherein said container comprises a dispensed liquid sample volume, and wherein a second electrode is arranged adjacent to the lower outside of said container, thereby forming a capacitor, measuring the capacitance of said capacitor, comprising the steps of, applying a sine-wave signal to said first electrode from a signal source, wherein the frequency of said sine-wave signal is selected so that the transfer function of the electrical circuit becomes frequency-independent, and measuring the output signal from said second electrode using a voltmeter;

determining the capacitance value of said dispensed liquid sample volume; and determining the volume of said dispensed liquid sample by comparing said capacitance value of said dispensed liquid sample volume with a calibration capacitance value.

28. The method of claim 27, wherein said sine-wave signal is free of frequency stabilization.

29. A method to determine a volume of dispensed liquid comprising:

inserting a first electrode into a well in a test plate, wherein said container comprises a dispensed liquid sample volume, and wherein a second electrode is arranged adjacent to the lower outside of said container, thereby forming a capacitor, measuring the capacitance of said capacitor, determining the capacitance value of said dispensed liquid sample volume, and determining the volume of said dispensed liquid sample by comparing said capacitance value of said dispensed liquid sample volume with a calibration capacitance value.

30. The method of claim 29, wherein said well is one of a plurality of wells arranged a two-dimensional array in said test plate.

31. The method of claim 30, wherein said capacitance value of said dispensed liquid sample volume is calculated by subtracting a reference capacitance value from said measured capacitance value.

32. The method of claim 31, wherein said reference capacitance value is an average capacitance value of said well with no liquid sample present, as determined from measurements on said well for a plurality of test plates with no liquid sample present.

33. A method to determine a volume of dispensed liquid comprising:

inserting a first electrode into a container, wherein said container comprises a dispensed liquid sample volume, and wherein a second electrode is arranged adjacent to the lower outside of said container, thereby forming a capacitor, measuring the capacitance of said capacitor, comprising the steps of applying an input signal to said first electrode from a signal source, and measuring the output signal from said second electrode using a voltmeter;

determining the capacitance value of said dispensed liquid sample volume, and determining the volume of said dispensed liquid sample by comparing said capacitance value of said dispensed liquid sample volume with a calibration capacitance value;

wherein said capacitance value of said dispensed liquid sample volume is calculated by subtracting a reference capacitance value from said measured capacitance value.

34. The method of claim 33, wherein said input signal is a time-dependent electrical signal.

35. The method of claim 34, wherein said time-dependent signal is a sine-wave signal.

* * * * *

UNITED STATES PATENT AND TRADEMARK OFFICE

CERTIFICATE OF CORRECTION

PATENT NO. : 8,468,885 B2
APPLICATION NO. : 12/664690
DATED : June 25, 2013
INVENTOR(S) : Berndt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 630 days.

Signed and Sealed this
Eighth Day of September, 2015

Michelle K. Lee

Michelle K. Lee
*Director of the United States Patent and Trademark Office*